United States Patent
Hénot et al.

(10) Patent No.: US 6,709,672 B2
(45) Date of Patent: *Mar. 23, 2004

(54) PHARMACEUTICAL OR FOOD COMPOSITION FOR TREATING PATHOLOGIES ASSOCIATED WITH GRAFT REJECTION OR AN ALLERGIC OR AUTOIMMUNE REACTION

(75) Inventors: Frédéric Hénot, Brussels (BE); Thierry Legon, Korbeek Lo (BE); Jean Duchateau, Soignies (BE); Geneviève Servais, Soignies (BE)

(73) Assignee: Biotech Tools S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/891,148

(22) Filed: Jun. 25, 2001

(65) Prior Publication Data

US 2002/0102632 A1 Aug. 1, 2002

Related U.S. Application Data

(63) Continuation-in-part of application No. 09/380,548, filed on Oct. 28, 1999, now Pat. No. 6,312,711.

(30) Foreign Application Priority Data

Mar. 5, 1997 (BE) ............................................. 9700199

(51) Int. Cl.$^7$ ................................................ A61K 39/00
(52) U.S. Cl. ................ 424/439; 424/184.1; 424/190.1; 424/434; 424/275.1; 424/193.1; 514/2
(58) Field of Search ............................. 424/439, 184.1, 424/190.1, 275.1, 193.1, 434; 514/2

(56) References Cited

U.S. PATENT DOCUMENTS 6,017,540 A    1/2000   Srivastava et al. ....... 424/193.1
6,312,711 B1 * 11/2001  Duchateau et al. ......... 424/439
6,433,141 B1 *  8/2002  Wallen et al. .............. 530/350

FOREIGN PATENT DOCUMENTS

| WO | WO94/29459 | 12/1994 |
| WO | WO95/24923 | 9/1995 |
| WO | WO96/13723 | 5/1996 |
| WO | WO96/36880 | 11/1996 |
| WO | WO97/06821 | 2/1997 |
| WO | WO98/23735 | 6/1998 |

OTHER PUBLICATIONS

Barrios et al., "Mycobacterial heat–shock proteins as carrier molecules . . ."*European Journal of Immunology*, 1992, vol. 22, p. 1365–1372.

Michilis et al., "Fine Tuning of Epitopic Dominance Induced by Lung Cancer on the IgG Response to Bovine Batalactoglobulin," *Cancer*, Feb. 15, 1996, vol. 77, No. 4, pp. 657–664.

Strobel et al., "Immune responses to dietary antigens: oral tolerance," *Immunology Today*, Apr. 1998, vol. 19, No. 4, pp. 173–181.

(List continued on next page.)

Primary Examiner—Thurman K. Page
Assistant Examiner—Liliana Di Nola-Baron
(74) Attorney, Agent, or Firm—Merchant & Gould, P.C.

(57) ABSTRACT

The present invention is related to a process for obtaining a composition comprising peptides bound to one or more heat shock protein(s) and for possibly recovering from said composition the bound peptides, wherein the peptides resulting from a previously in-vitro hydrolysis of at least one immunogenic and antigenic macromolecular structure, are mixed in-vitro with one or more heat shock protein(s).

Figure 1:
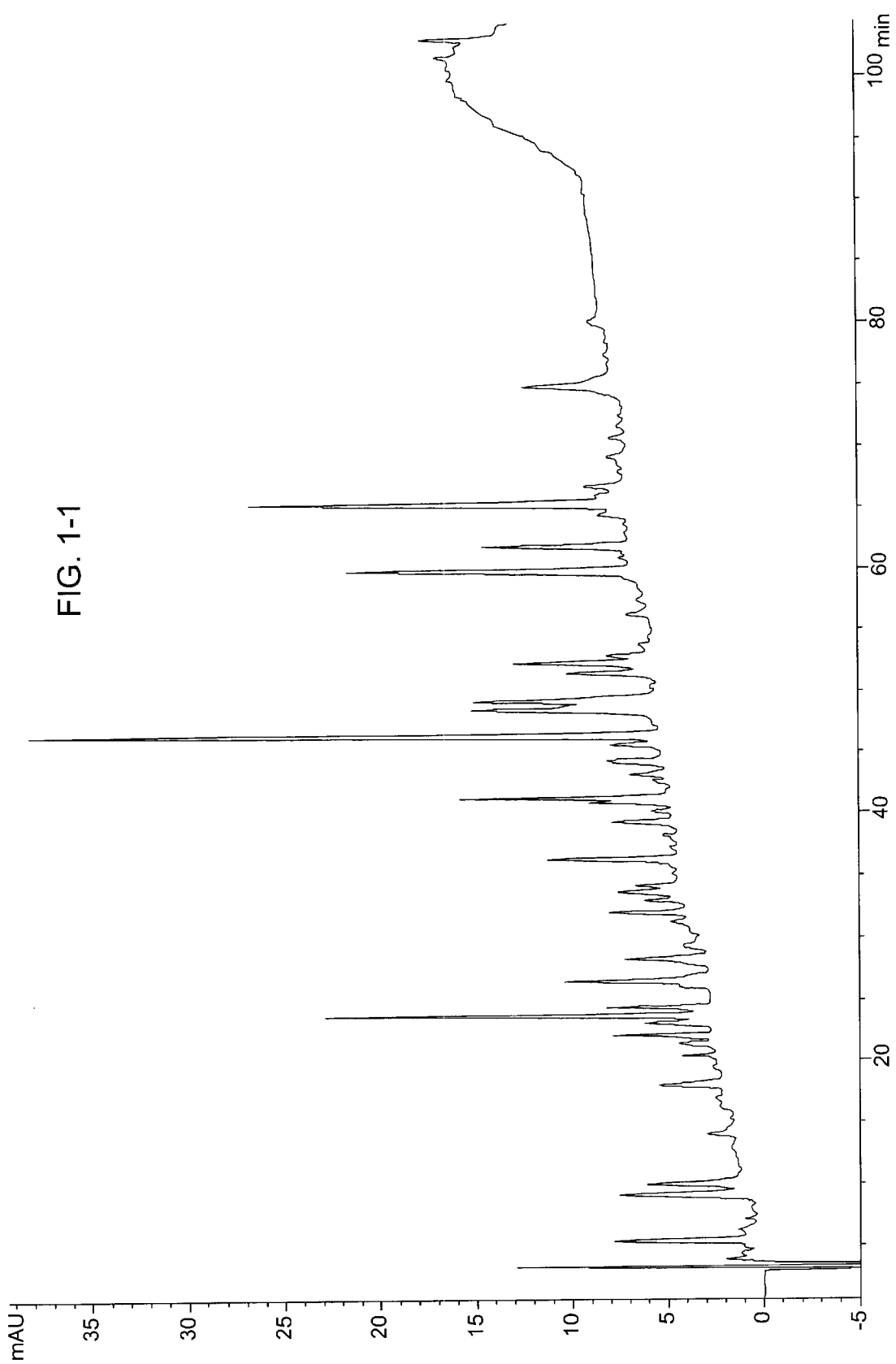

The present invention is also related to the compositions obtained by said process.

20 Claims, 20 Drawing Sheets

OTHER PUBLICATIONS

McGhee et al., "Mucosal Immune Responses: An Overview," *Mucosal Immunology*, 1999, pp. 485–506.

Pharmacia & Upjohn, *Pharmacia Cap System Allergens*.

Hendrick et al., "Molecular Chaperone Functions of Heat–Shock Proteins," *Annual Review of Biochemistry*, 1993, vol. 62, pp. 349–383.

Roitt, *Essential Immunology*, 1988, Blackwell Scientific Publications, Oxford.

Polla et al., "Presence of hsp65 in bacterial extracts (OM–89): a possible mediator of orally–induced tolerance?".

XP–002083262; Self and Foreign 60–Kilodalton Heat Shock Protein T Cell Epitope Peptides Serve As Immunogenic Carriers for a T Cell–Independent Sugar Antigen; Stephanie Konen–Waisman, Mati Fridkin, and Irun R. Cohen; Department of Organic Chemistry and Department of Cell Biology, The Weizmann Institute of Science, Rehovot, Israel; pp. 5977–5985; Mar. 10, 1995.

* cited by examiner

PHARMACEUTICAL OR FOOD COMPOSITION FOR TREATING PATHOLOGIES ASSOCIATED WITH GRAFT REJECTION OR AN ALLERGIC OR AUTOIMMUNE REACTION

This application is a Continuation-In-Part of U.S. patent application Ser. No. 09/380,548, now U.S. Pat. No. 6,312,711, filed on Oct. 28, 1999.

SUBJECT OF THE INVENTION

The present invention relates to a novel pharmaceutical or food composition intended for treating pathologies associated with graft rejection or an allergic or autoimmune reaction.

TECHNOLOGICAL BACKGROUND OF THE INVENTION

In the last twelve years, controlled studies have described desensitization based on the oral administration of allergens (1). This method is based on the fact that the oral administration of an antigen facilitates the acquisition of an immunological tolerance to it. The digestive route constitutes the mode of contact of the body with antigens, of food or microbial origin. However, allergic reactions are rare. Oral administration of sheep red blood cells (SRBC) to rats prevents the rats from later producing anti-SRBC antibodies after a subcutaneous injection, whereas, without the prior oral intake, the allergic response would have been present. This phenomenon constitutes what is referred to immunologically as oral tolerance.

This oral desensitization method has been validated in prospective and controlled studies, and makes it possible to reduce the risks of anaphylaxis, in particular for birch pollen and acari. It is already available on the vaccines market in a presentation in drinkable form (sold by the company Laboratoire des Stallergénes—Paris).

Moreover, it may be considered that the benefit, in terms of protecting infants against allergy to milk, which has been observed since the introduction of new, enzymatically pre-digested powdered milk formulations, would result from the induction of immunological tolerances by the presentation of antigens in the form of peptides.

Document WO-A-95/24920 describes the use of complexes consisting of the combination of a stress protein and a peptide as a prophylactic or therapeutic vaccine against intracellular pathogens.

That document does not in any way describe the possibility of using such complexes in vivo in the treatment of autoimmune or allergic diseases or graft rejections.

In the third paragraph of page 10, that document describes that said immunogenic and antigenic macromolecular structures can be associated with autoimmune or allergic diseases, and that, in this case, said antigen is administered in combination with said stress proteins in an amount which is sufficient to generate tolerance or to inhibit a pre-existing immune response against said antigen in an individual.

It is indicated that the amount of stress proteins required to inhibit this immune response is assumed to be substantially larger than the amounts required to obtain a stimulation.

However, it is difficult to predict or state the efficacy of the desensitization. Clinical observation makes it possible, after the event, to confirm or deny any improvement in the symptoms.

It is known, from international patent application WO 96/36880, to be able to detect and/or quantify ligands specific to a pathology associated with an allergic or autoimmune response or lung cancer, by means of a test of competition between ligands present in a sample and other discriminable ligands. This test is based on the fact that allergic and symptomatic individuals recognize, by means of their antibodies, epitopes different from those recognized by the antibodies of tolerant individuals on the same specific immunogenic and antigenic macromolecular structure of said pathology. That document also describes the possibility of measuring the evolution of this specificity, in particular in the case of children who are allergic to milk and the change toward the in vivo acquisition of tolerance to milk.

Patent application WO94/29459, "Stress proteins and uses thereof" relates to a stress protein and methods of modulating an "individual" immune response. It also relates to a composition comprising a stress protein joined to another component, such as a fusion protein in which a stress protein is fuse to an antigen. According to the invention, it is possible to modulate the immune response in an individual, such as a human, other mammals or other vertebrates by altering the individual's response to stress protein. By altering the individual's immune response to the stress protein, it is possible to enhance or induce an individual's response to a pathogen or to cancer cells or enhance or induce an up-regulation of an individual's immune status and to decrease an individual's autoimmune response, such as it occurs in some forms of arthritis.

U.S. Pat. No. 6,048,530 "Stress protein-peptide complexes as prophylactic and therapeutic vaccines against intracellular pathogens" describes a family of vaccines that contain stress protein-peptide complexes which, when they are administered to a mammal, are operative to initiate in the mammal a cytotoxic T cell response against cells infected with a pre-selected intracellular pathogen. The patent also discloses the preparation of stress protein and immunogenic stress protein-peptide complexes from infected cells or tissues, the isolation of potentially immunogenic peptides from stress protein-peptide complexes from infected cells or from MHC-peptides complexes. The synthesis of those peptides and the reconstitution of heat shock protein-peptide complexes with synthetic peptides or peptides isolated from heat shock protein-peptide complexes isolated from infected cells is also described. According to said document, the peptides-heat shock protein complexes, when isolated from a eukaryotic cell infected with a pre-selected intracellular pathogen, and then administered to a mammal can stimulate a cytotoxic T cell response against cells infected with the same pathogen.

Patent application WO97/06821 "Heat shock protein-based vaccines and immunotherapies" describes a composition for inducing a therapeutic immune response in a subject, comprising: a) a target antigen; and b) a heat shock protein; wherein the target antigen and the heat shock protein are combined in vitro under conditions wherein binding of target antigen to the heat shock protein occurs to form a target antigen-heat shock protein complex; wherein the administration of the target antigen/heat shock protein complex to the subject induces an immune response comprising a cytotoxic cellular component.

Patent application WO98/23735 "Immune responses using compositions containing stress proteins" describes a vaccine for inducing a cell-mediated cytolytic immune response in a mammal against an antigen. The vaccine is comprising the antigen and all or a portion of stress protein or all or a portion of a protein having an amino acid sequence sufficiently homologous to the amino acid sequence of the stress protein to induce the immune response against the antigen. In one embodiment, the antigen is an antigen of the influenza virus. In another embodiment, the antigen is a tumor-associated antigen. The patent also describes a mixture of known allergenic antigens (allergens) and stress proteins or compositions containing allergens chemically linked or fused to the stress protein. Allergens used in allergen-stress protein fusion proteins are necessarily of a peptidic nature; non peptidic allergens can be used in conjugates containing an allergen and a stress protein or a mixture of allergens and stress proteins. Non limiting examples for allergens include Fel d1 (cat), . . .

Epitope mapping technology is the identification and localization of the specific regions of macromolecules that are recognized by the immune system. An epitope is a small region of a macro molecule that the immune system recognizes and responds to. T cell epitopes are linear fragments of the original protein molecule whereas B cell epitopes can be either linear fragments or folded three-dimensional regions of the intact macro molecule.

Several methods for epitopes mapping have been previously described:

Classical Epitope Mapping

Defined fragments of the cDNA for the antigens of interest are expressed as recombinant (fusion)proteins and probed with autoantisera in various assays such as Western blot or ELISA.

Phage Display Technology

Small random fragments of the cDNA for the antigen of interest are cloned into the phage protein pIII or pVIII of the filamentous phage and are displayed on the surface of the phage. Epitope-displaying phages can be captured with antibodies in a procedure called "bio-panning". Sequencing of the inserts of the corresponding phages gives some information on the epitopes. This procedure is in principle capable to identify conformational epitopes.

Peptide Scan Technology

Small overlapping oligopeptides that ideally cover the complete amino acid sequence of the antigen of interest are synthesized on a solid support and probed with antisera. This method allows the identification of linear epitopes on the amino acid level. It also allows rapid mutational studies.

Prior art provides neither a method to prepare in-vitro a mixture between at least one heat shock protein and peptides resulting from the in-vitro hydrolysis of at least one immunogenic protein, nor a method to identify from such a mixture the peptides that can bind to the stress proteins and/or the peptides that do not bind to the stress protein.

Prior art describes neither compositions according to the invention comprising a mixture of at least one heat shock proteins and peptides resulting from the in-vitro hydrolysis of at least one immunogenic protein and antigenic macromolecular structure, nor a method to prepare such a composition.

Prior art describes neither compositions according to the invention comprising a mixture of heat shock proteins, complexes between the heat shock proteins and the peptides resulting from said in-vitro hydrolysis, and free peptides resulting from the in-vitro hydrolysis nor a method to prepare such a composition.

Prior art describes neither a composition according to the invention comprising purified complexes between heat shock proteins and some of the peptides resulting from said in-vitro hydrolysis nor a method to prepare such a composition.

Prior art describes neither compositions according to the invention comprising peptides that do not bind to heat shock proteins, these peptides resulting from the said in-vitro hydrolysis nor a method to prepare such a composition.

Prior art describes neither compositions comprising the peptides isolated from the complexes made between Heat Stock Proteins (HSP) and peptides resulting from said in-vitro hydrolysis nor a method to prepare such a composition.

Aims of the Invention

The aim of the present invention is to provide a novel composition, which may be of pharmaceutical or food type, designed to modify the immune response of patients toward a pathology associated with an allergic or autoimmune reaction or toward graft rejection phenomena, such that the immune response of said patients comes close to the natural tolerance manifested by normal individuals (who remain free of symptoms although they are also liable to be exposed to this pathology).

The present invention is also directed toward providing an inexpensive pharmaceutical or food composition which is easy to administer and which can be used in a prophylactic and/or therapeutic manner.

A further aim of the invention is to provide with an easy, reliable and fast method to prepare in vitro, characterize and possibly recover immunogenic peptides. The invention is based on mixing in vitro at least one heat shock protein with peptides resulting from a in-vitro hydrolysis of at least one immunogenic and antigenic macromolecular structure.

Another aim of the invention is to provide with an easy, reliable and easily up-scalable method to prepare in-vitro and to characterize and possibly to recover a mixture of at least one heat shock protein with peptides resulting from the in-vitro hydrolysis of the said immunogenic and antigenic macromolecular structure.

Another aim of the invention is to provide with a method to separate and recover the peptides that do not bind to heat shock protein and the peptide-heat shock protein complexes, from a mixture according to the invention. Another aim of the invention is to characterize and possibly recover such unbound peptides.

Another aim of the invention is to provide with a method to isolate from the peptides-heat shock protein complexes according to the invention, the peptides that bind to the heat shock protein, to characterize and possibly to recover such peptides.

Characteristic Elements of the Invention

The present invention relates to a pharmaceutical or food composition comprising an adequate pharmaceutical or food vehicle, a stress protein (also known as "heat shock protein" or HSP) and at least one of the epitopes (conformational or sequential epitope) of an immunogenic and antigenic macromolecular structure, said structure inducing graft rejection, an allergic reaction or an autoimmune reaction. Preferably, the pharmaceutical or food vehicle of the composition is adequate for mucosal (in particular oral) or cutaneous administration.

Advantageously, the stress protein and the epitope naturally form in vitro a complex naturally (i.e. without formation of a covalent bond), as described by Roamn et al., Febs (1994), Fouri et al., The Journal of Biological Chemistry, Volume 269 No. 48, pp. 30470–30478 (1994), Palleros et al., The Journal of Biological Chemistry, Volume 269 No. 48, pp. 13107–13114 (1994), Grageroov and Gottesman, Journal of Molecular Biology, No. 241, pp. 133–135 (1994), and Schmid et al., Science, Volume 260, p. 1991 (1994) incorporated below by way of reference.

Advantageously, the stress protein is a bacterial stress protein present, for example, in saprophytic bacteria, such as *E. coli.*

Among the stress proteins of the present invention, mention may be made of the stress protein GroEL, the stress proteins GrpE, DnaK or DnaJ as described in particular by Hendrick and Hartl (Annual Review of Biochemistry, No. 62, p. 349 (1993)) or the heat shock proteins HSP 60, 70, etc.

The expression "phenomenon of graft rejection or allergic or autoimmune reaction" means hypersensitivity reactions of immediate or delayed type brought about by contact in particular with an allergen (this reaction can be immediate and specific (anaphylaxis, urticaria, etc.) or delayed over time) or autoimmune diseases and disorders of the immune system of immediate or delayed type associated with graft rejections of host against graft type and graft against host type.

Autoimmunity is a state of immunization of an individual against his or her own constituents, and the phenomenon of graft rejection is a state of immunization of an individual against foreign constituents (bodily fluids such as blood, cerebrospinal fluid, etc., cells, tissues, organs, antibodies, etc.) deliberately implanted into the patient. These phenomena are observed in particular in pathologies selected from the group consisting of infections associated with SLE (Systemic Lupus Erythematosus disease), Gougerot-Sjögren syndrome (or Sjögren's disease) and rheumatoid polyarthritis, as well as pathologies such as sarcoidosis and osteopenia, spondylarthritis, scleroderma, multiple sclerosis, amyotrophic lateral sclerosis, hyperthyroidism, Addison's disease, autoimmune hemolytic anemia, Crohn's disease, Goddpasture's syndrome, Graves' disease, Hashimoto's thyroiditis, idiopathic purpural hemorrhage, insulin-dependent diabetes, myasthenia, pemphigus vulgaris, pernicious anemia, poststreptococcal glomerulonephritis, psoriasis and spontaneous sterility, as well as immediate or delayed phenomena observed during graft rejections.

The expression "immunogenic and antigenic macromolecular structure which induces graft rejection or an allergic or autoimmune reaction" means macromolecules such as allergens made of peptides, lipides, polysaccharides and/or nucleic acids, preferably selected from the group consisting of the major allergic antigens present in chemicals (latex), in foods such as eggs, soya and milk, in particular bovine beta-lactoglobulin (BLG) from cow's milk, the major allergic antigens present in plants, molds, medicaments (in particular antibiotics or vaccines) and pollens, the major allergic antigens present in animals, in particular in hairs, and venom, in particular wasp and other insects venom, the major antigens of the allergic reaction to acari, to the mite present in house dust (antigen P1 Dermatophagoides pteronyssinus), the major antigen of *Aspergillus fumagatus,* and staphylococcal enterotoxin B (SEB).

Other non-limiting examples of allergens or mixtures of allergens have also been described in the publication ISBN-91-970475-5-4 by Pharmacia AB, which is incorporated herein by way of reference.

The "macromolecular structure" can also be an antigenic complex made of peptides, liquids, saccharides and/or nucleic acids which induces an autoimmune disease. Preferably, this immunogenic and antigenic macromolecular structure is specific to lupus (SLE) or Sjögren's disease, in particular the plasma membrane or a portion of this membrane containing membrane DNA with a weight of greater than 100 KD, in particular as described in patent application WO 96/13723, the publication number of which is incorporated by way of reference.

Other non-limiting examples of antigenic complexes which induce autoimmune diseases have also been described by Roitt I. M. (Essential Immunology, Blackwell Scientific Publication (ch. 14) ISBN 0-632-01994-8) and by Humbel R. L. (Auto-anticorps et maladies auto-immunes [Autoantibodies and autoimmune diseases], Ed. Scientifiques Elsevier (1994) ISBN 2-906077-58-5).

This immunogenic and antigenic macromolecular structure can also be major histocompatibility loci (MHC I and/or MHC II) or minor histocomptability immunogenic and antigenic macromolecular structures present at the surface of blood cells and involved in the induction of the immune system (or portions thereof), which are specific to an individual and are involved in graft rejection phenomena (including bodily fluid transfusions).

The appropriate pharmaceutical or food vehicle according to the present invention may be any suitable additive or support, such as a nontoxic compatible substance for administration of the composition according to the invention to a patient. The type of appropriate pharmaceutical or food vehicle used will depend on the mode of administration selected. In particular, for oral administration, these vehicles can consist of aqueous solutions, syrups, lozenges, capsules, etc. Other pharmaceutical vehicles such as creams or ointments may be selected depending on the type of administration, in particular for cutaneous administrations.

A person skilled in the art can also adapt the pharmaceutical vehicle as a function of a subcutaneous, intradermal, intravenous, intramuscular or parenteral administration, via nasal or oral inhalation, etc.

The peptide and epitope according to the invention are advantageously (possibly) added to a specific emulsion composition, more preferably an oil in water emulsion which is suitable for specific mucosal administrations (especially an oral administration).

The percentage of active compound present in the composition according to the invention will depend on the type of patient, the pathology treated and the route of administration. The doses will be limited only by the patient's tolerance to the product, as well as by the administration rates.

The administration concentrations will be chosen in particular such that the abovementioned pathological signs and symptoms are reduced, preferably eliminated, by the administration doses envisaged by the posology. The preferred concentrations for a human are: mg(active compounds)/Kg (patient).

The inventors have discovered, unexpectedly, that the use of the pharmaceutical and/or food composition according to the invention makes it possible to modify the immune response of a patient induced with said immunogenic and antigenic macromolecular structure. The modification of a patient's immune response can be detected and quantified in particular according to the process and technique described in patent application WO 96/36880 or by any method of clinical analysis of the treated patient (including prophylactic methods) which is well known to those skilled in the art.

Another aspect of the present invention relates to the use of the composition according to the invention for the preparation of a medicament designed to modify a patient's immune response toward an immunogenic and antigenic macromolecular structure which induces graft rejection or an allergic or autoimmune reaction. In particular, the present invention relates to the use of the pharmaceutical and/or food composition according to the invention for the preparation of a medicament intended to desensitize atopic or non-atopic allergies.

Another aspect of the present invention relates to the use of the pharmaceutical and/or food composition according to the invention for the preparation of a medicament intended for the prevention or treatment of the abovementioned allergic reactions and autoimmune diseases, for the treatment or prevention of graft rejections, optionally in combination with a specific product for reducing or neutralizing allergic reactions, autoimmune reactions and graft rejection phenomena (in particular the administration of immunosuppressants such as azathioprine, steroids, antilymphocyte globulins, cyclosporin A, rapamycin, FK-506 (tacrolimus) or lymphokines (in particular IL-10), and the analogs and agonists thereof which are well known to those skilled in the art.

The terms "analogs" and "agonists" of these molecules means other molecules, or derivatives of these molecules, which act on the same receptor or via the same mechanism of action as the abovementioned specific products.

The present invention also relates to a process for the therapeutic or prophylactic treatment of a patient, comprising the step of administration of the composition according to the invention to said patient so as to modify the patient's immune response toward an immunogenic and antigenic macromolecular structure which induces graft rejection or an allergic or autoimmune reaction.

The invention is related to any product comprising a mixture of at least one carrier molecule selected from the group consisting of heat shock proteins, antibodies, major locus histocompatibility complex (MHC) or similar molecules and peptides resulting from the in-vitro hydrolysis of at least one immunogenic protein.

The invention is related to any product comprising a mixture according to the invention of:
  peptides resulting from said in-vitro hydrolysis of at least one immunogenic protein,
  complexes between said carrier molecule and the peptides resulting from said in-vitro hydrolysis
  uncomplexed carrier molecules.

The invention is also related to any product comprising purified complexes between at least said carrier molecule and peptides resulting from said in-vitro hydrolysis.

The invention is related to any product comprising the peptides isolated from the complexes between a said carrier molecule and peptides resulting from the said in-vitro hydrolysis.

The invention is also related to any pharmaceutical or food compositions comprising any product according to the invention. In a preferred embodiment, the products according to the invention are associated with immuno-modulators like but not limited to cytokines, anti-cytokines, corticoids, vaccine adjuvants, antibodies, thymic peptides, nanoparticles, emulsions and liposomes. In another embodiment, the composition comprise at least two carrier molecules complexes according to the invention.

The invention is also related to any pharmaceutical or food compositions according to the invention able to enhance an immune response against the entire protein through, but not limited to, T-cells cytotoxic immune response or to down-regulating immune response against the entire protein or any autoimmune diseases associated protein through, but not limited to, the mechanisms described by H. L. Wiener in Encyclopedia of Immunology, $2^{nd}$ edition Academic Press (Ed P. J. DELVE & I. M. ROITT) pages 1893–1899 or by W. O Weigle in Encyclopedia of immunolgy $2^{nd}$ edition Academic Press (Ed P. J. DELVE & I. M. ROITT) pages 2359–2361 or by D. W Scott in Encyclopedia of Immunology $2^{nd}$ edition Academic Press (Ed P. J. DELVE & I. M. ROITT) pages 2362–2367. In a preferred embodiment the tolerance mechanism is a low dose mechanism. In another preferred embodiment the composition according to the invention induces TGF-β producing T-cells named Th3 T-cells.

The invention is also related to any diagnosis kit including any product according to the invention. In a preferred embodiment, the product according to the invention included in the diagnosis kit comprises at least two peptides-carrier molecule complexes according to the invention.

In a preferred embodiment of the invention, the proteins are:
  any protein or other macromolecular structure or recombinant protein or mutated protein or combination thereof related to an autoimmune disease among other insulin, thyroglobulin, type II collagen, gliadin, GAD65, proteolipid protein, S-antigen, acetylcholin receptor, haptenized colonic proteins, interphotoreceptor retinoid binding protein, myelin, peripheral nerve P2, LDL, HDL
  any protein or other macromolecular structure or recombinant protein or mutated protein or combination thereof related to allergy like the allergens according to Diagnostic Testing of Allergic disease Clinical Allergy and Immunology S. F. Kemp & R. F Lockey ISBN 0-8247-0303-0 pages 13–44.
  any protein or other macromolecular structure or recombinant protein or mutated protein or combination thereof related to allograft and/or xenograft rejection like xenoantigen, alloantigen, MHC-peptides and blood group antigens.
  any protein or other macromolecular recombinant protein or mutated protein or combination thereof from pathogens responsible of any infectious or parasitic diseases like virus, bacteria, fungi, protozoa and helminth.
  any carrier molecule (heat shock protein related to autoimmune diseases or any recombinant protein or mutated protein or combination thereof or blood proteins).

In another preferred embodiment, the macromolecular structure, especially the protein, the recombinant protein, the mutated protein or the combinations thereof are extensively washed in an adequate solution through, but not limited to, ultra-filtration or dialysis to remove any low molecular weight material loosely associated with it.

Hydrolysis can be performed by enzymatic digestion with at least one protease or other suitable enzyme of any living organism. The proteases could be selected among the list according to the Nomenclature Committee of the International Union of Biochemistry and Molecular Biology at http://www.chem.qmw.ac.uk/iumbmb/enzyme/EC34, and the list of the MEROPS database http://www.merops.co.uk and of the Rawlings N D and Barrel A J MEROPS: the peptidase database; Nucl. Acids Res. 28 323–325 (1998), and of Barret A J, Rawlings N D Woessner J F (eds) 1998 Handbook of Proteolytic Enzymes, Academic Press London.

In a preferred embodiment, macromolecular structures, especially proteins, known to be resistant to in-vitro or in-vivo hydrolysis are denatured either by physical (e.g. heating, high mechanical pressure) or by chemical methods (e. g. reductive reagents, urea, guanidinium chloride).

In another preferred embodiment, the structures resistant to hydrolysis are allergens (e.g. OVA).

In another preferred embodiment, the macromolecular structures with a proteolytic activity are denatured or specifically inhibited before enzymatic digestion (e. g; Der p1).

Hydrolysis can also be performed with at least one chemical agent like, but not limited to, mild acid (70% formic acid at 40° C.), hydroxylamine, cyanogen bromide, iodosobenzoic acid or 2-nitro-5-thiocyanobenzoate followed by alkali.

In a preferred embodiment, the peptides or glycopeptides resulting from in-vitro hydrolysis of at least one macromolecular structure can be separated on the basis of their molecular weight e.g. by ultra-filtration or gel filtration or dialysis prior to the mixing with the heat shock proteins. In a preferred embodiment, the cut-off of the filter or of the membrane is about 10 kDa and at most 10 kDa (other suitable filters to be used have cut-offs of about 5 or 50 kDa).

In a preferred embodiment, the peptides or glycopeptides resulting from the in-vitro hydrolysis can be separated on the basis of their hydrophilic/hydrophobic properties e.g. by phase separation or solvent extraction before the mixing with the carrier molecule. Prior to the mixing with the carrier molecule, the organic phase is removed e.g. by solvent stripping or solvent evaporation or lyophilisation and hydrophobic peptides are dissolved in an adequate water solution e.g. a suitable buffer to make the complexes with the HSP.

In a preferred embodiment, the peptides or glycopeptides resulting from the in-vitro hydrolysis are bound to a solid support e.g. by covalent link, hydrophobic interactions, interactions between biotin or biotin derivatives and an avidin selected among the avidin protein families.

Characterization of the peptides or glycopeptides resulting from said hydrolysis can be performed either by ion exchange chromatography, or by gel electrophoresis, gel filtration or electro-elution, or by reverse phase high pressure liquid chromatography (HPLC).

Peptides that were bound to the HSP can be individually collected after HPLC or ion exchange chromatography elution, or by gel electrophoresis, gel filtration or electroelution.

N-terminal peptides sequence analysis can be performed by procedures based upon the Edman degradation reaction. C-terminal peptides sequence analysis can be performed by using non specific carboxypeptidases (A, B, P, Y) . In another embodiment said peptide sequence can be performed by mass spectrometry analysis (e. g. MALDI or MALDI-TOF or ESI or LC-MS or MS/MS or FAB).

Peptides-carrier molecule complexes according to the invention can be characterized directly from the crude mixture by mass spectrometry e.g. MALDI or MALDI-TOF.

Carrier molecules, especially the heat shock proteins according to the invention are molecular chaperones according to Mary-Jane Gething "Guidebook to molecular chaperones and protein folding catalysts" A Sambrook & Tooze publication at Oxford University Press and "Molecular Chaperones and Folding Catalysts—Regulation, Cellular Function and Mechanisms" B. Bukau—Harwood Academic publishers. In a preferred embodiment of the invention, the heat shock proteins are purified and depleted of any boundpeptides according to the method known by the person skilled in the art, e.g. incubation in a low-pH buffer or in an ATP-containing buffer.

In another preferred embodiment, the heat shock proteins are partial or total recombinant heat shock proteins or any homologous sequences of said HSP described previously. In another preferred embodiment the heat shock protein are microbial heat shock protein (bacteria, fungi and yeast).

In a preferred embodiment, the carrier molecules are bound to a solid support, e.g. by covalent links, hydrophobic reactions, interactions between biotin and biotin derivatives and an avidin chosen among the avidin protein families, gelatin, ATP- or ADP affinity column.

The mixture is obtained by mixing in vitro at least one solution of peptides resulting from an in vitro hydrolysis of at least one protein with at least one solution containing at least one carrier molecule. In this case it is bound to a solid support, at least one solution of peptides resulting from the hydrolysis of at least one carrier molecule is put into contact with the solid support. In the case of peptides resulting from the in-vitro hydrolysis of at least one protein are bound to a solid support, at least one solution of at least one carrier molecule is put into contact with the solid support. In a preferred embodiment, the mixing is performed under conditions allowing the formation of peptide-carrier molecule complexes. Such conditions are described in the prior art.

The compositions according to the invention are prepared as a galenic form to modulate the immune response.

EXAMPLES

Example 1

Epitopes Mapping

Materials
  Laboratory bench microcentrifuge
  Water bath 37° C.
  Water bath 25° C.
  Water bath 20° C.
  Centricon YM- 10 (Millipore)
  Tris.HCl 20 mM pH 8.0
  Tris.HCl 1.0 M pH 6.8
  Distilled water pH 2.0 (pH adjusted with HCl 0.1 N)
  HEPES 25 mM ; KCl 10 mM ; $MgCl_2$ 3 mM ; β-mercaptoethanol 5 mM ; pH 7.5 buffer 1
  ATP (Sigma, A-2383)
  ADP (Sigma, A-6646)
  Pepsin (Sigma, P-6887)
  Trypsin, TPCK-treated (Sigma, T-1426)
Proteins of Interest
  Bovine beta-lactoglobulin (Sigma, L-0130) or BLG
  Bee venom phospholipase A2 (Sigma, P-9279) or PLA2
  Myelin basic protein (Sigma, M-1891) or MBP
  rec Alt a1 (recombinant allergan of Alternaria altemata)
(Biomay
  Productions und HandelsgesmbH, Dr Bohr-Gasse 7b, A-1030 Wien)
  rec Bet v1a (recombinant allergen of birch) (Biomay Productions)
HSP Preparation
  The DnaK protein was purified from *E coli* BR1640 transformed with the plasmid BR1639/pBM19 carrying the coding sequence of DnaK. DnaK was purified from a crude extract of the bacteria grown in LB medium containing tetracyclin. Protein expression was induced with 1 mM IPTG during four hours. The protein was purified according to the literature in three steps (ion exchange chromatography, hydroxyapatite column and gel filtration) . The purity of the protein was checked by a SDS page gel electrophoresis. Overloading of the gel with the protein shows a purity of at least 98%.
Protein Preparation
  The protein of interest is extensively washed with distillated water pH 2.0 in case of pepsin digestion or with trypsin digestion buffer in case of trypsin digestion by centrifugation through a centricon YM-10 assembly to remove any low molecular weight material loosely associated with it.

Pepsin Digestion

One to five milligrams of the protein of interest is dissolved in 1 to 5 mL of distilled water pH 2.0 (final concentration of 1 mg/mL). The solution is incubated for 10 minutes at 100° C. The solution is then rapidly cooled at 4° C., and 20 to 100 μL of pepsin solution (10 mg/mL of distilled water pH 2.0, final ration protein/protease of 0.2) is added to the protein solution. The resulting solution is incubated at 37° C. for six hours. A 200 μl aliquote is removed at the end of the incubation and placed into 200 μL of 20 mM Tris.HCl pH 8.0. The sample is then centrifuged through a centricon YM-10 assembly to remove the remaining protein and pepsin.

Trypsin Digestion

One to five milligrams of the protein of interest is dissolved in 1 to 5 mL of Tris.HCl 40 mM pH 8.0 (final concentration of 1 mg/mL). The solution is incubated for 10 minutes at 100° C. The solution is then rapidly cooled at 4° C., and 18 to 90 μL of β-mercaptoethanol is added (1.8% v/v). The resulting solution is incubated at 37° C. for 10 minutes and 20 to 100 μL of trypsin solution (10 mg/mL of Tris.HCl 40 mM pH 8.0, final ration protein/protease of 0.2) is added to the protein solution. The resulting solution is incubated at 37° C. for six hours. The solution is then centrifuged through a centricon YM-10 assembly to remove the remaining protein and trypsin.

DnaK.ATP Complex Preparation

25 μL of ATP solution (4.5 mg/mL of buffer 1) is added to 400 μL of DnaK (2 mg/mL of buffer 1). The solution is incubated at 20° C. for one hour, and then is centrifuged through a centricon YM-10 assembly to remove any low molecular weight material loosely associated with DnaK. The large molecular weight fraction is removed, and washed extensively with buffer 1 by ultrafiltration using a centricon YM-10.

In Vitro Production of Stress Protein-Peptide Complexes. Isolation of the Bound Peptides The ultrafiltrated and neutralized pepsin or trypsin digestion is mixed with the ATP-pretreated DnaK to give at least a 1:1 (w:w) DnaK:peptides ratio. Then, ADP is added (1 mM final) and the mixture is incubated for one hour at 25° C. in the suitable buffer 1. The preparations are centrifuged through a centricon YM-10 assembly to remove the remaining unbound peptides. The low and the large molecular weight fractions are recovered. The large molecular weight fraction containing DnaK-peptide complexes is washed extensively with buffer 1 containing 1 mM ADP by ultrafiltration using a centricon YM-10. The bound peptides are eluted by incubating the HSP-peptide complexes in a low pH buffer. A last ultrafiltration using a centricon YM-10 is removing the large molecular weight fraction. The incubation of the chaperone in ATP solution is not required to form complexes between chaperones and peptides.

HPLC Analysis

The resulting low molecular weight fractions are fractionated by reverse phase high pressure liquid chromatography (HPLC) using a Vydac C18 reverse phase column (HP32, 201TP52 C18, 250/2.1 mm,5 μm) equilibrated with buffer A (49.5% H$_2$O; TFA 0.5/1000 v/v). The bound material is eluted at a flow rate of 0.2 mL/min by developing the column with a step gradient of 0 to 100% of buffer B (1.0% CH$_3$CN; TFA 0.45/1000 v/v). The elution of the peptides can be monitored at both OD 214 nm and OD 280 nm.

Characterization

Peptides that were bound to DnaK can be individually collected after HPLC elution. Both their mass and aminoacid sequences can be determined.

The FIGS. 1 to 5 present the results of reverse-phase HPLC separation of peptides. Chromatograms generated by monitoring absorption at 214 nm. BLG: beta-lactoglobulin; PLA2: phospholipase A2 from bee venom; MBP:myelin basic protein; Alt a2=major allergen of Altemaria Alternata; Bet 1a=major allergen of Birch.

FIG. 1.1: peptides (MW< or =10 kDa) generated by pepsin-cleavage of PLA2.

FIG. 1.2: unbound peptides (MW< or =10 kDa) to DnaK, from the pepsin-cleavage of PLA2

FIG. 1.3: pepsin generated-PLA2 peptides (MW< or =10 kDa) that were bound to DnaK.

Figures 1, 2:
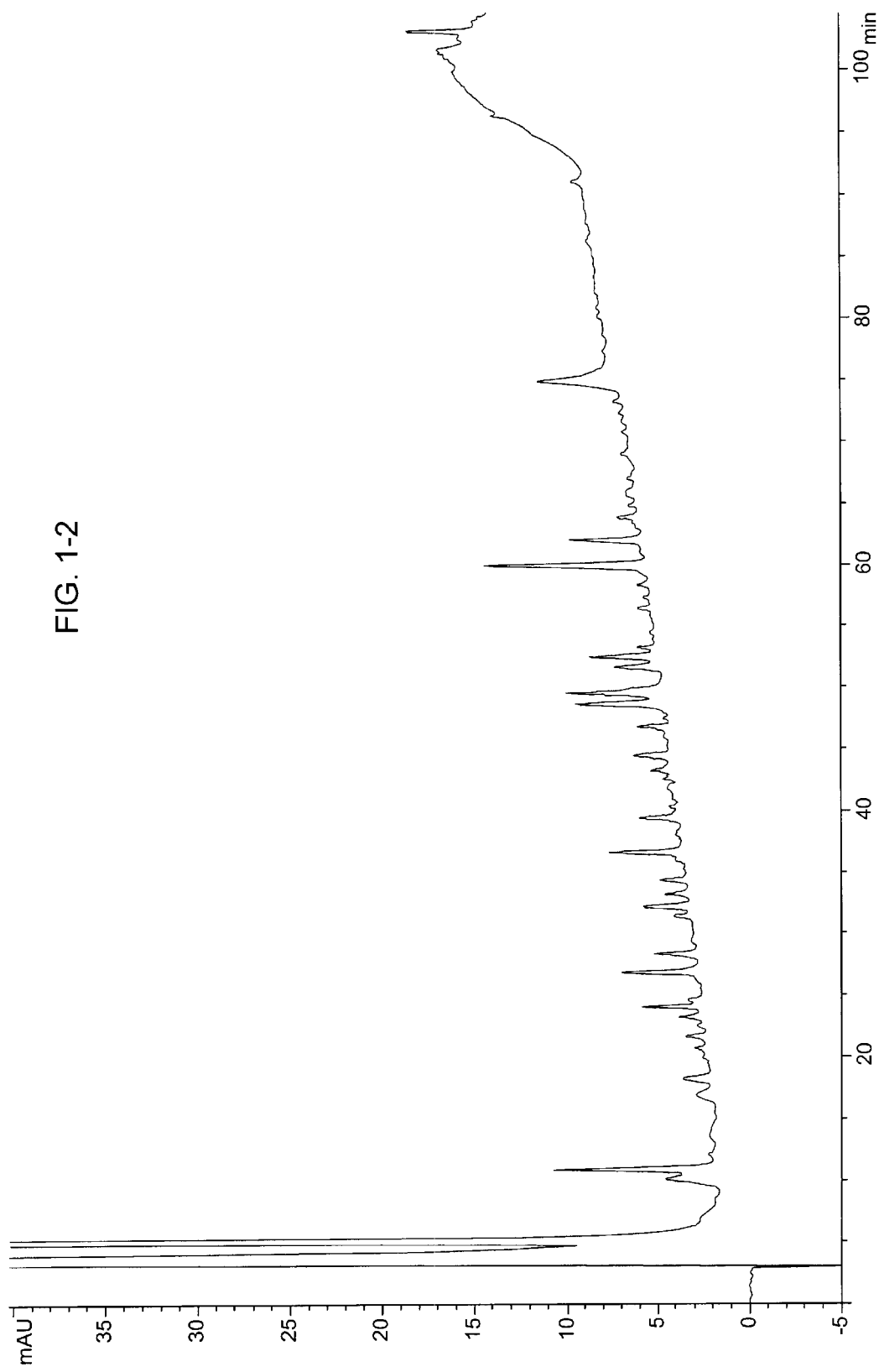

FIG. 2.1: peptides (MW< or =10 kDa) generated by pepsin-cleavage of MBP.

FIG. 2.2: unbound peptides (MW< or =10 kDa) to DnaK, from the pepsin-cleavage of MBP FIG. 2.3: pepsin generated-MBP peptides (MW< or =10 kDa) that were bound to DnaK.

Figures 1, 2, 3:
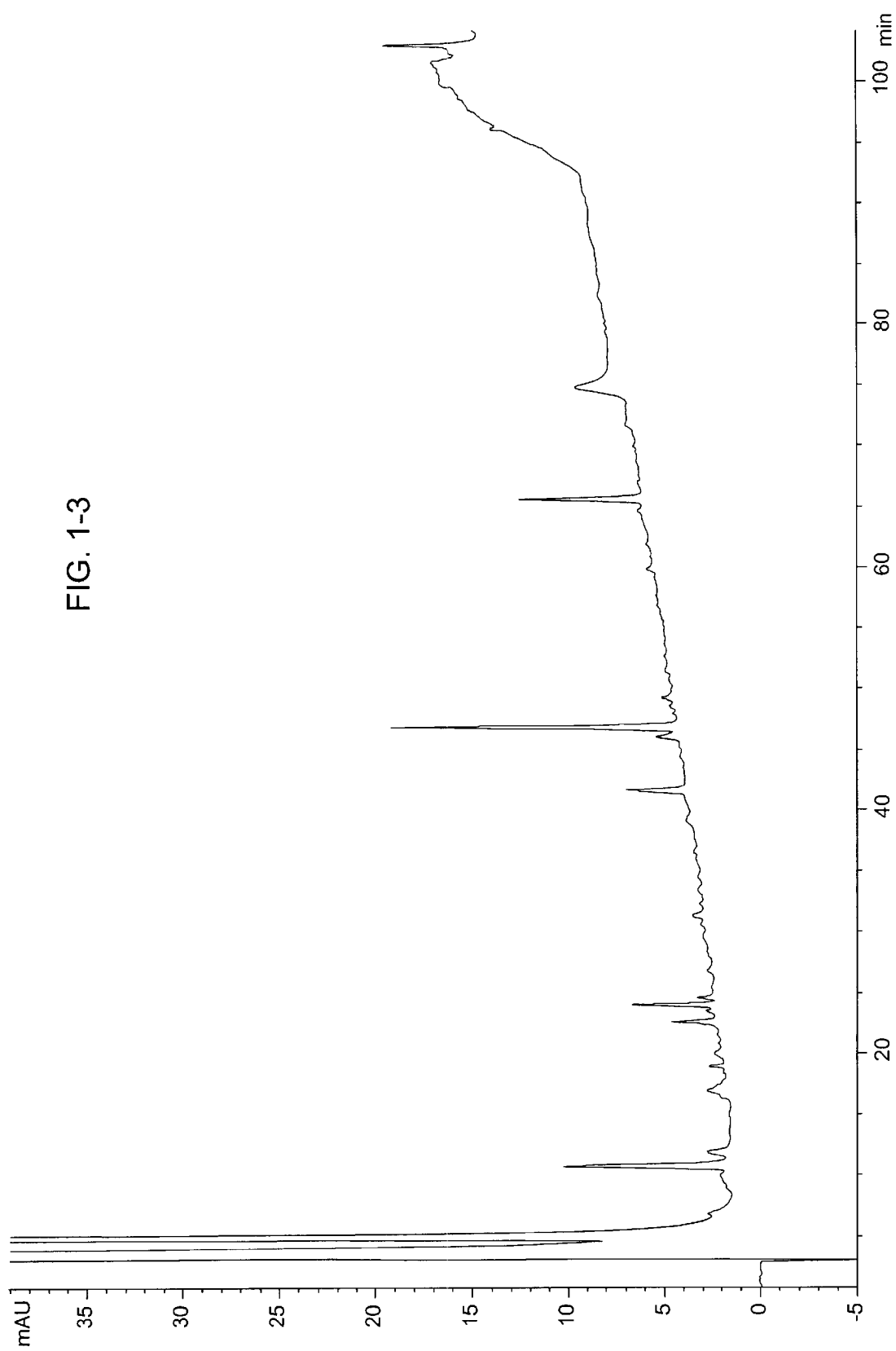
Figures 1, 2:
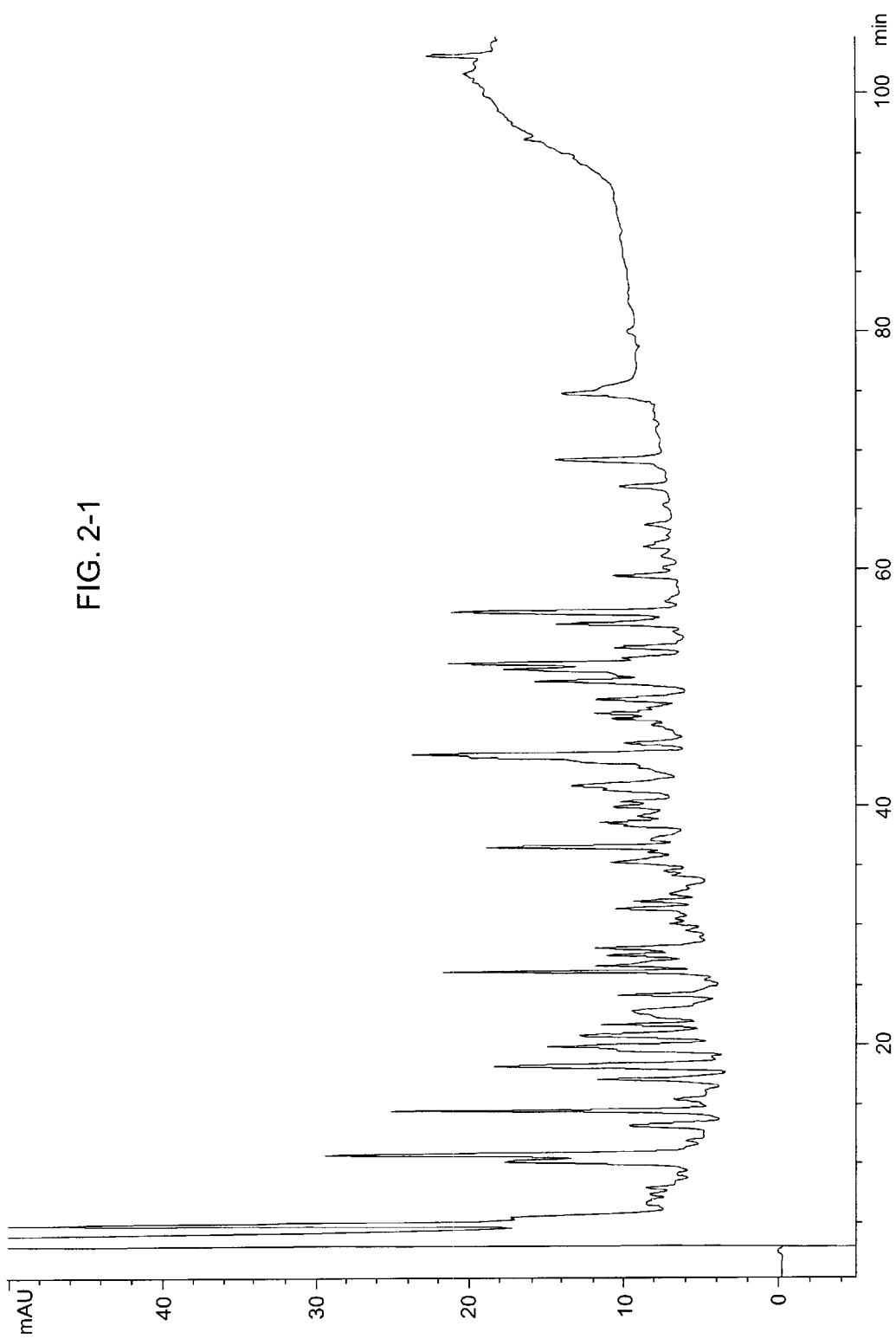
Figure 2:
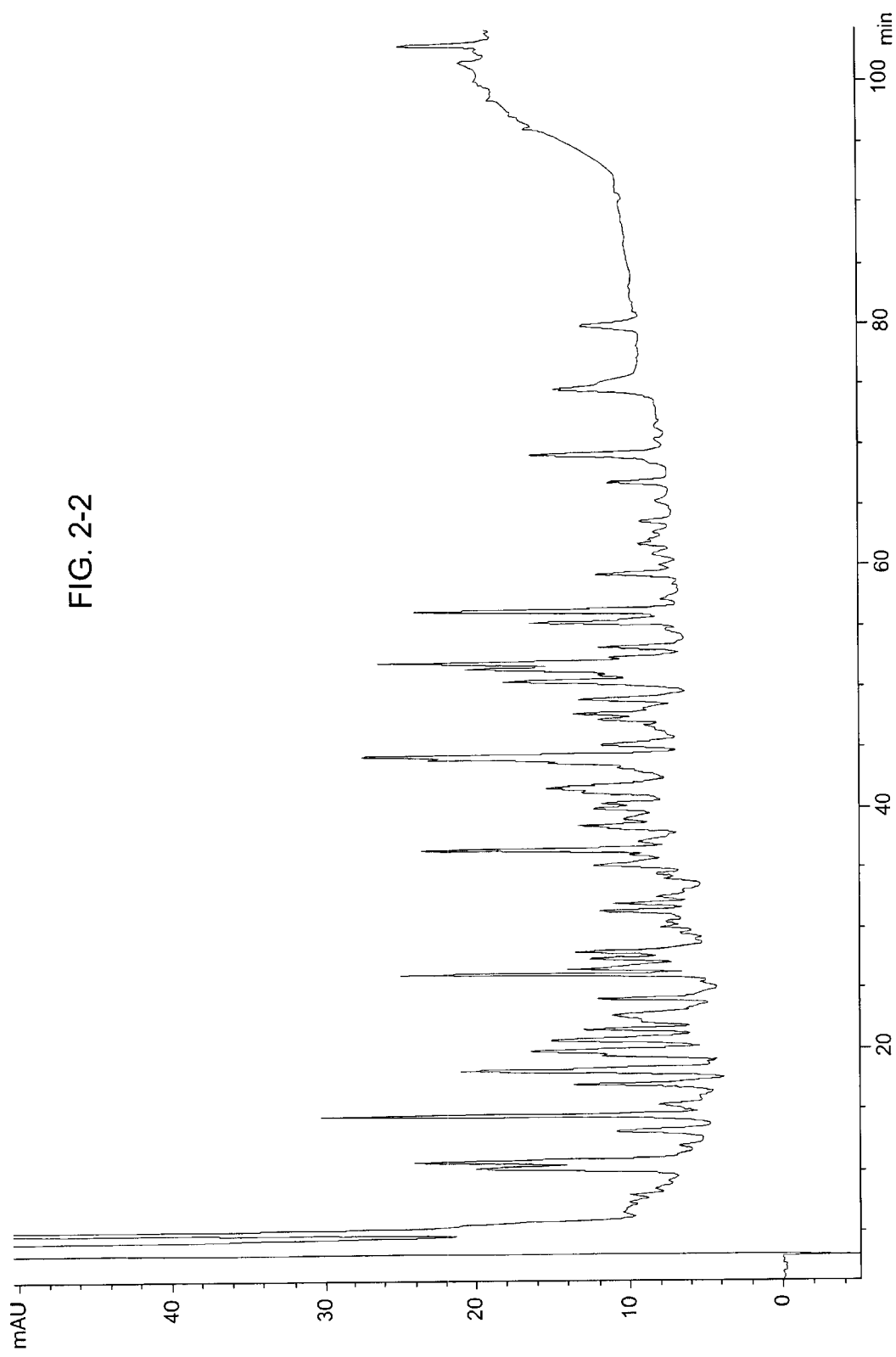
Figures 2, 3:
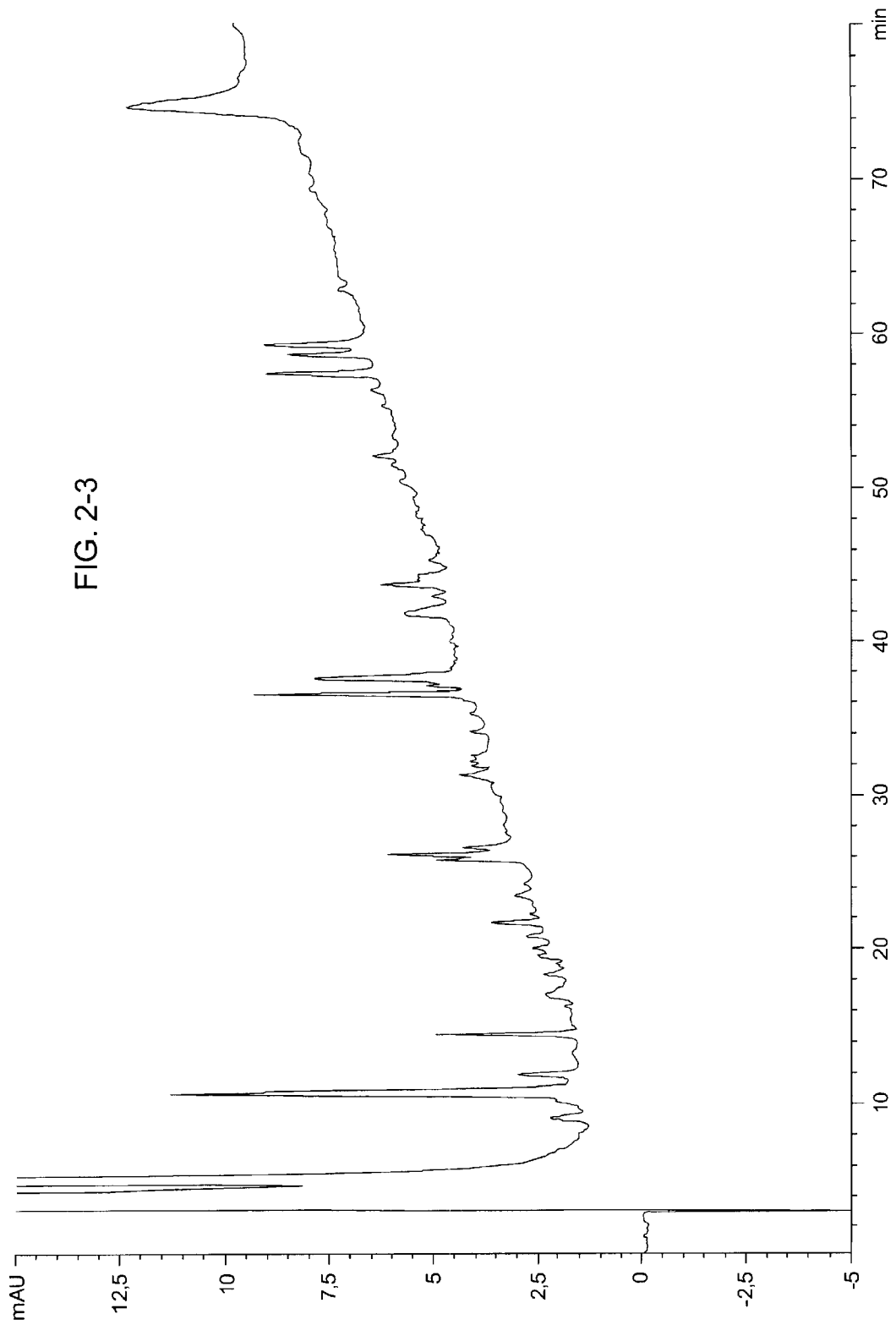
Figures 1, 3:
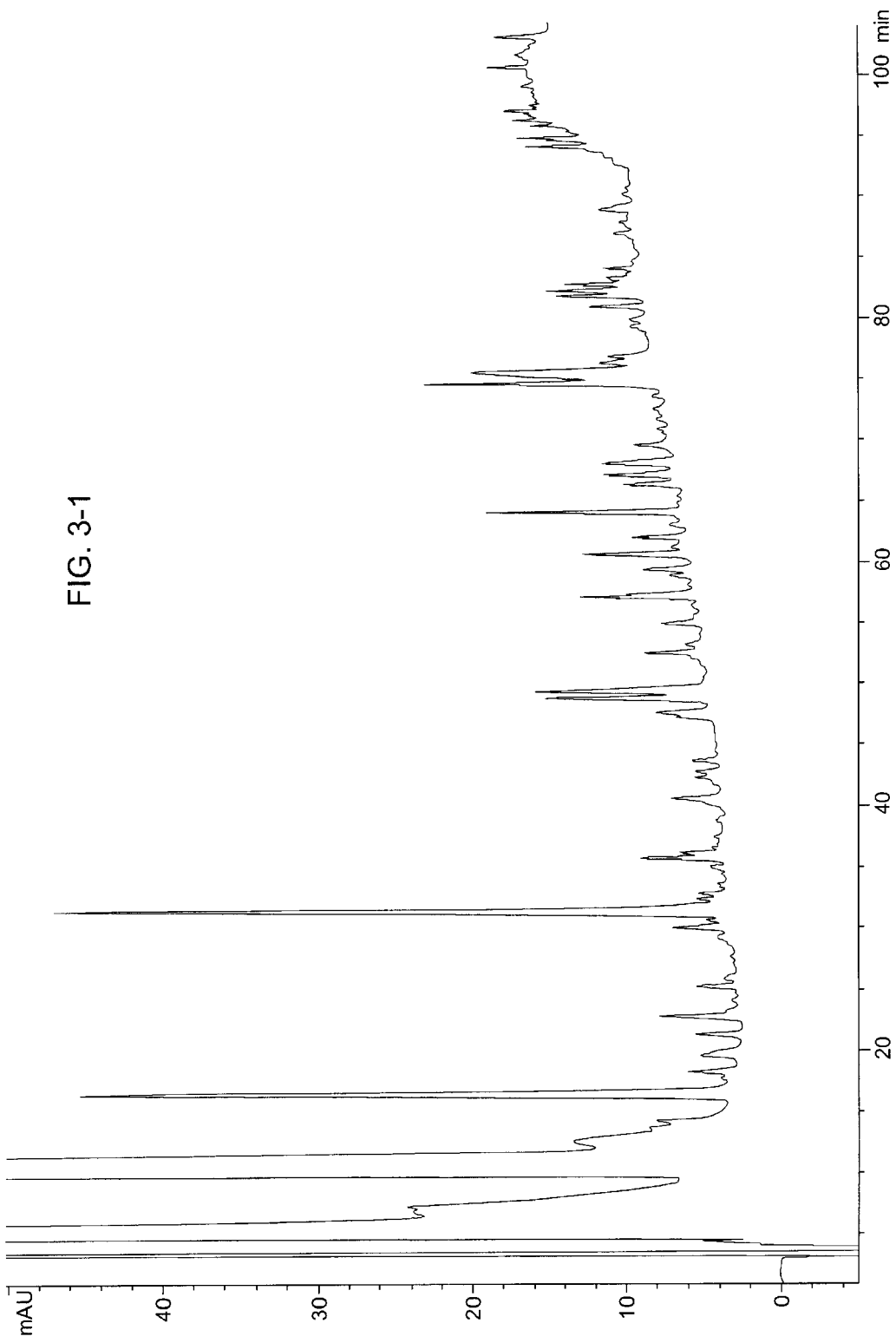
Figures 2, 3:
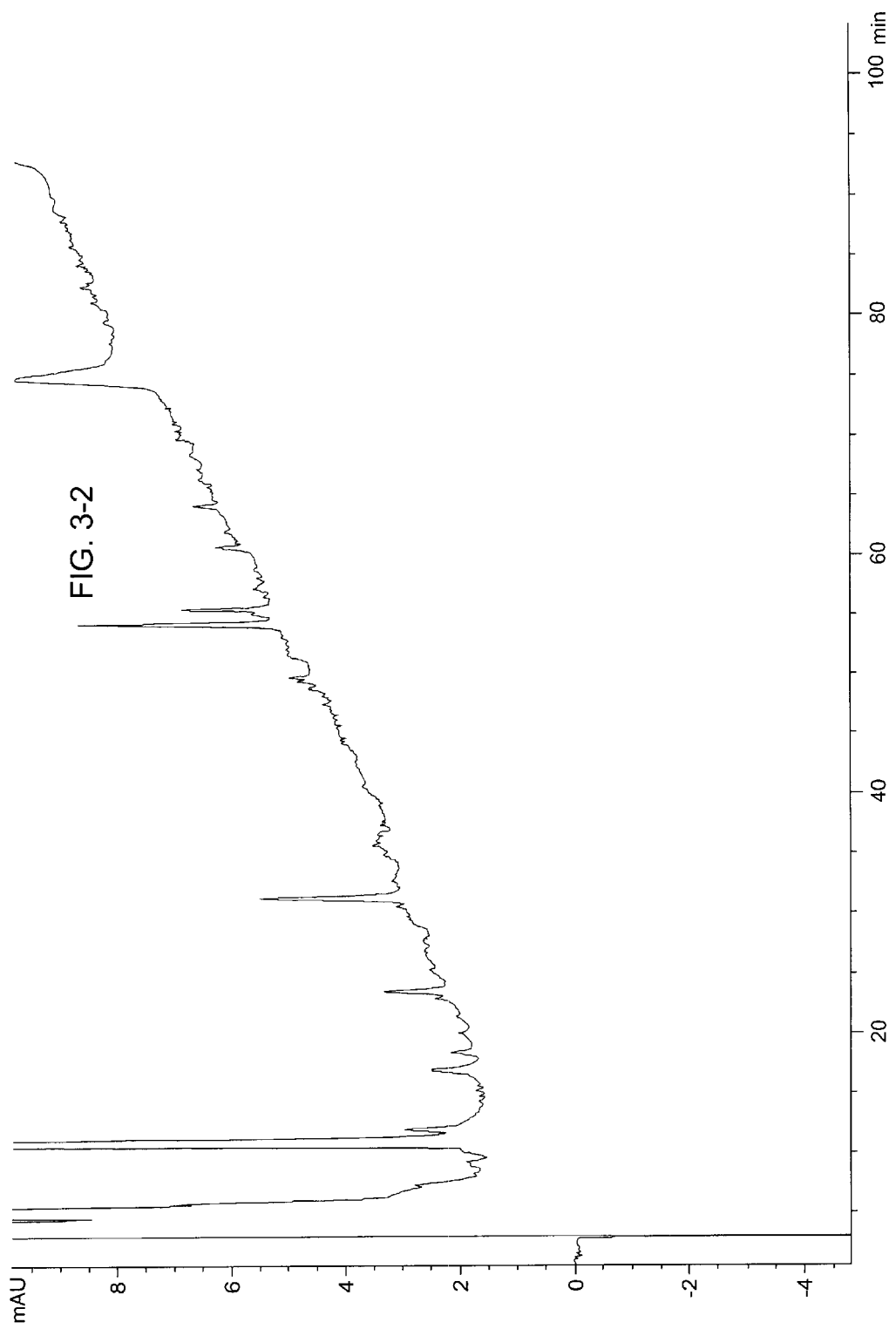

FIG. 3.1: peptides (MW< or =10 kDa) generated by trypsin-cleavage of BLG.

FIG. 3.2: trypsin generated-BLG peptides (MW< or =10 kDa) that were bound to DnaK.

Figures 1, 4:
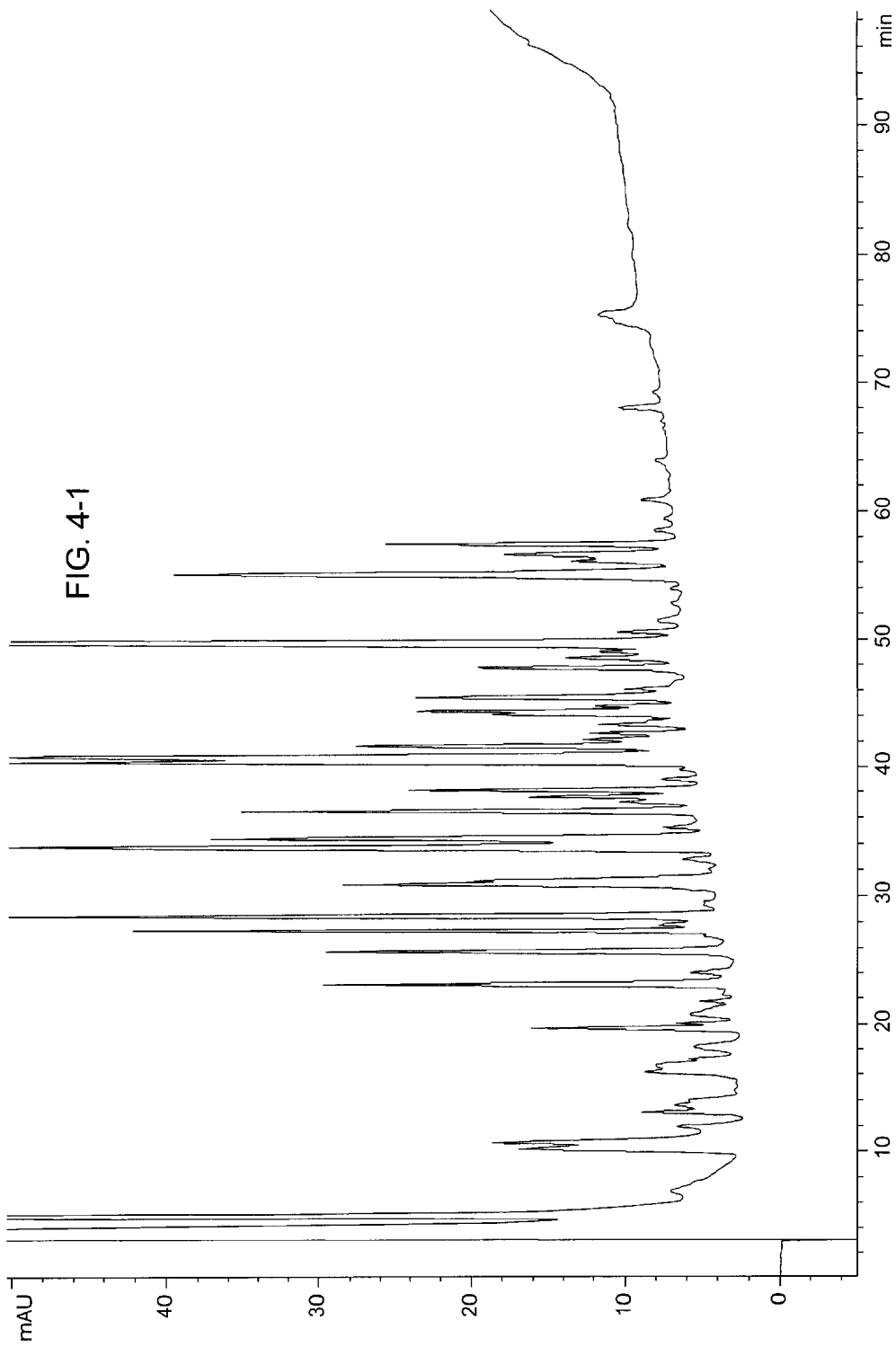
Figures 2, 4:
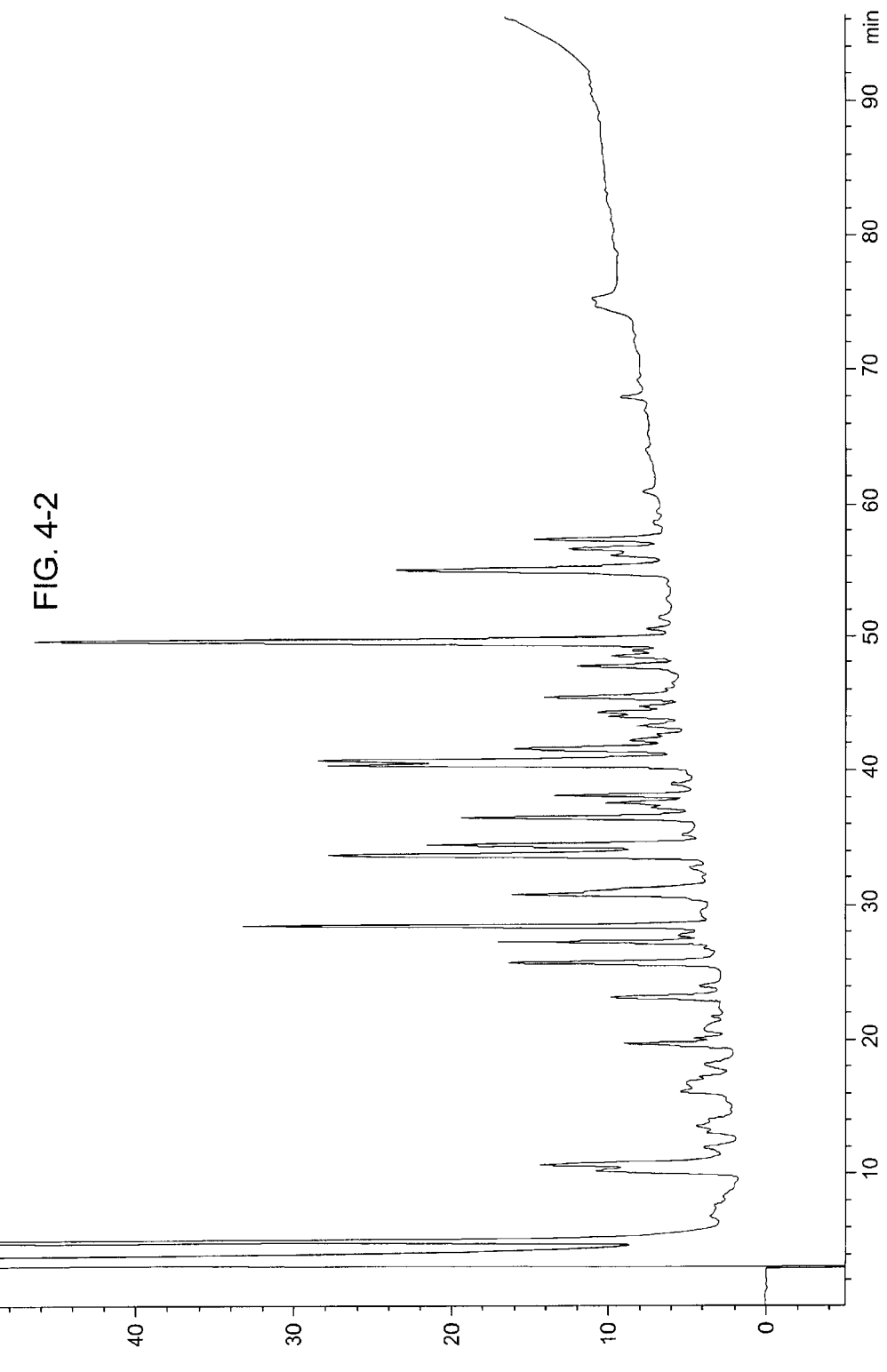
Figures 3, 4:
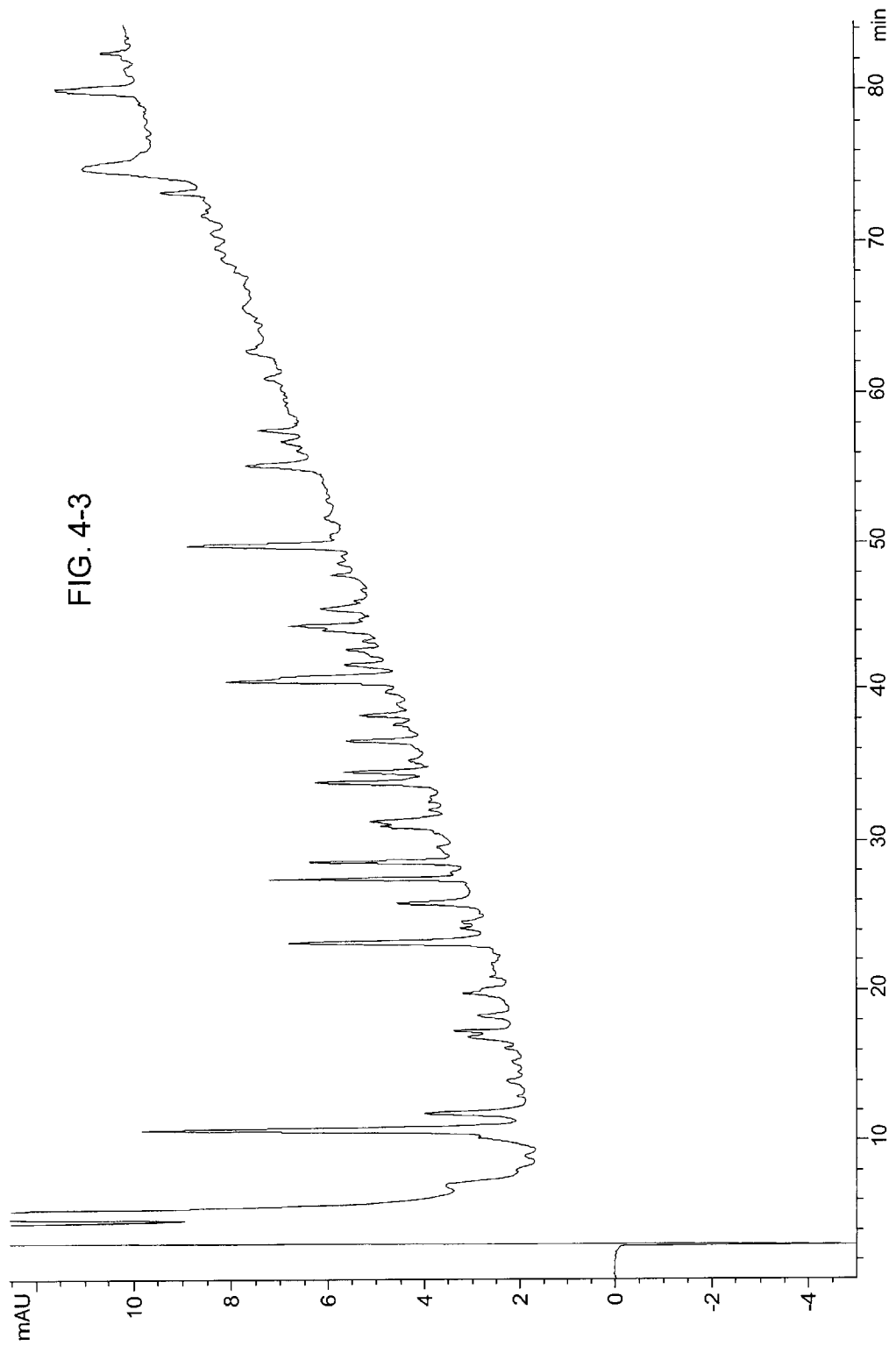

FIG. 4.1: peptides (MW< or =10 kDa) generated by pepsin digestion of Alt a 1.

FIG. 4.2: unbound peptides (MW<=10 kDa) to Dna-K, from the pepsin cleavage of Alt a 1.

FIG. 4.3: pepsin generated-Alt a 1 peptides (MW<=10 kDa), that were bound to DnaK.

Figures 1, 5:
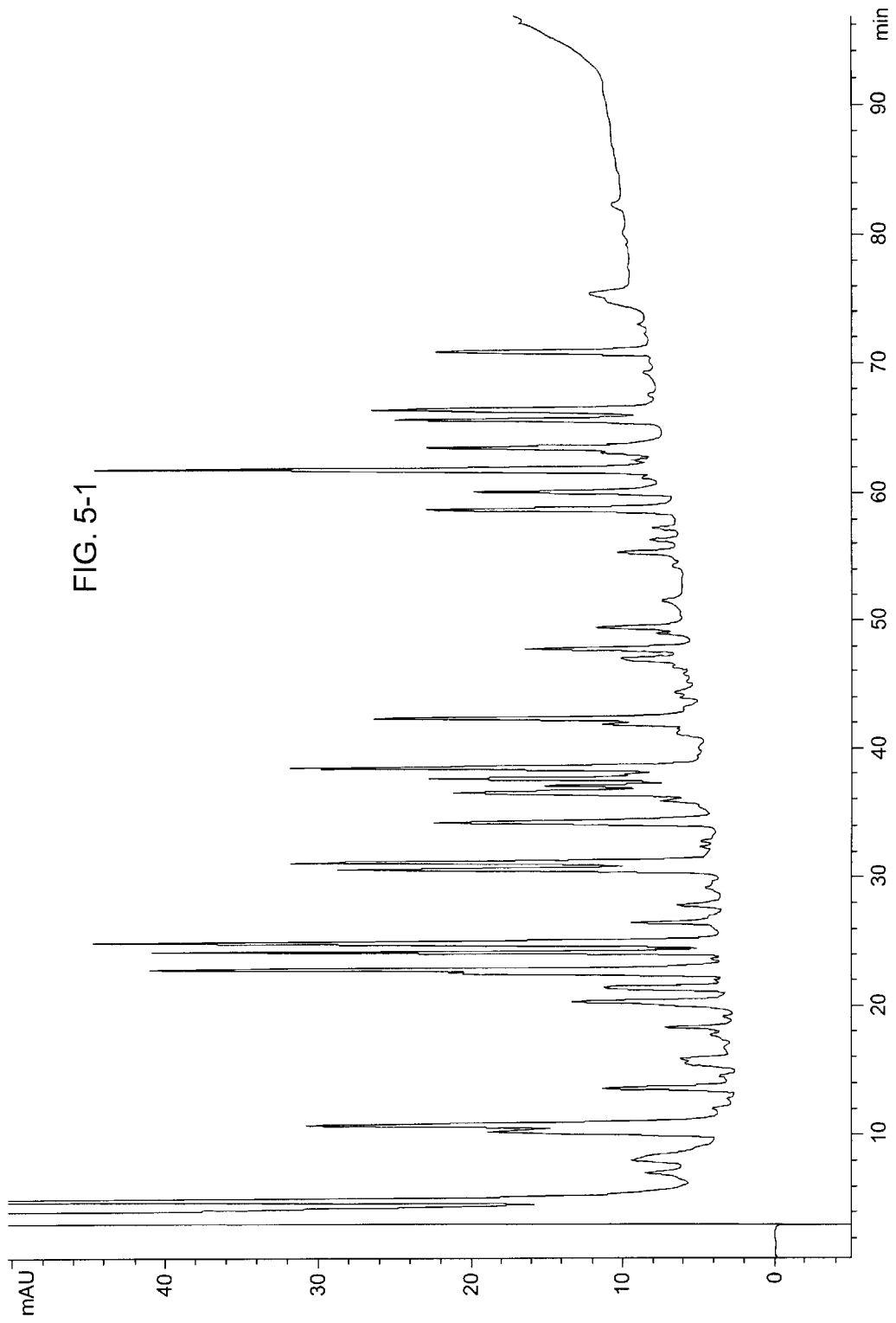
Figures 2, 5:
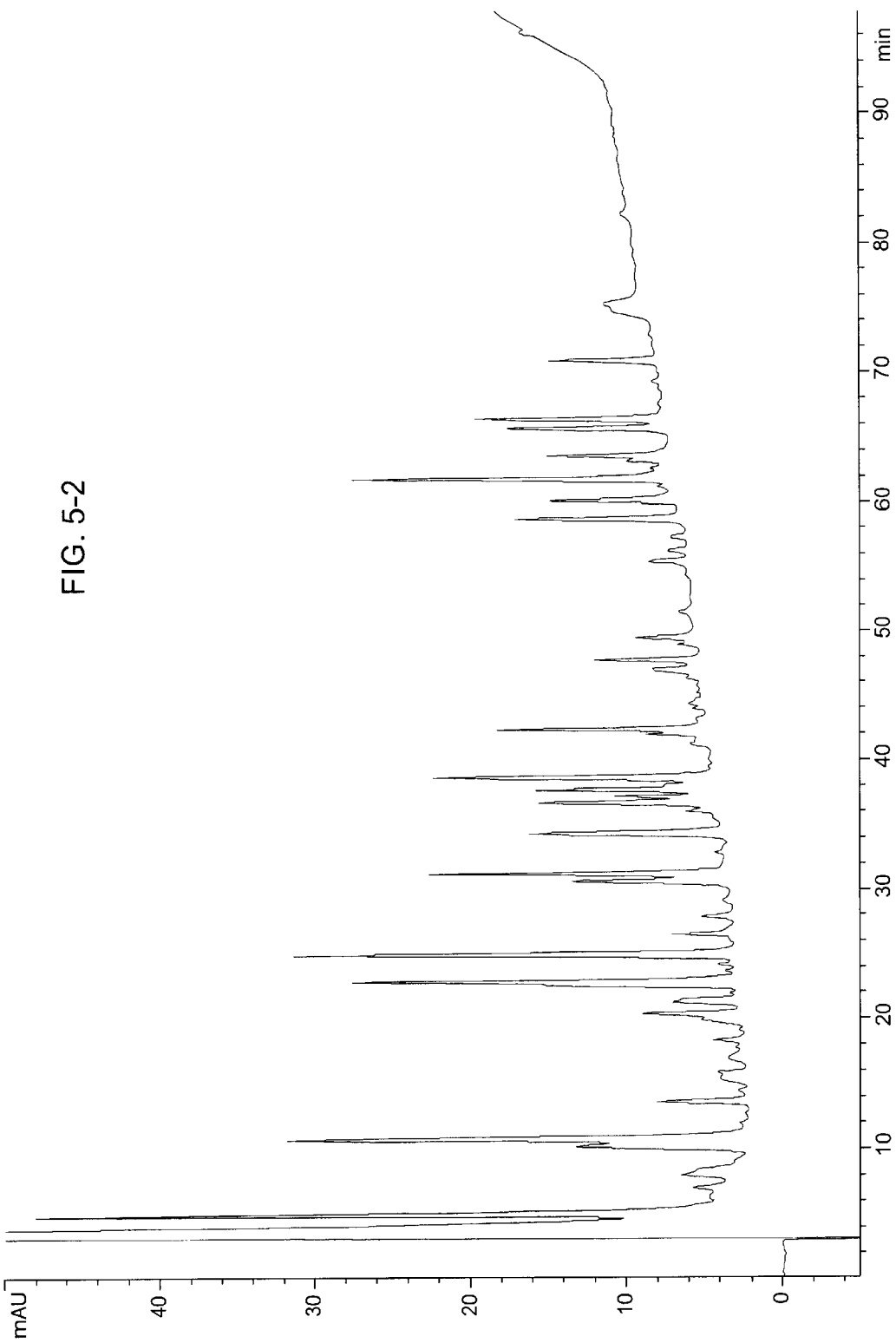
Figures 3, 5:
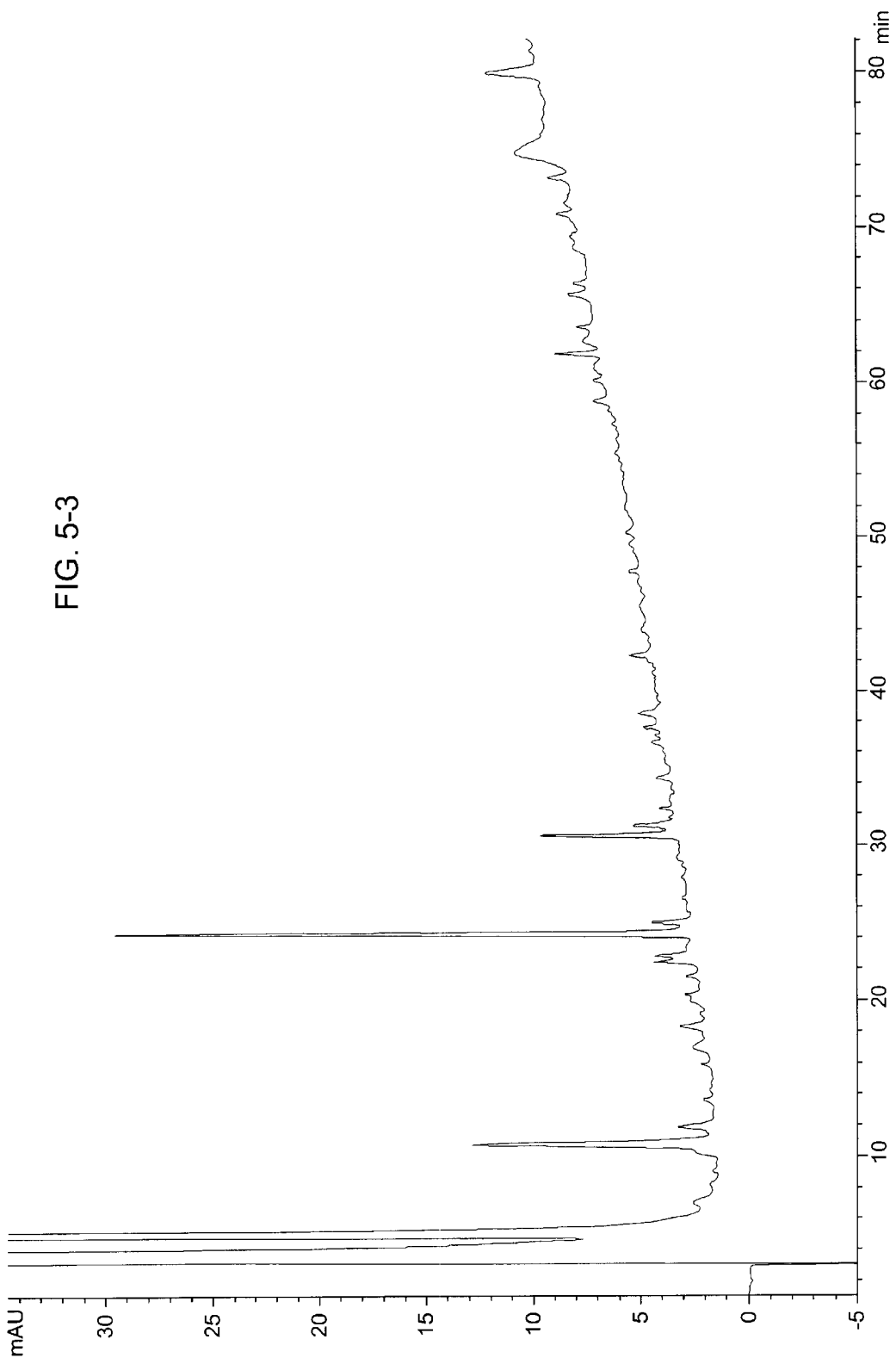

FIG. 5.1: peptides (MW< or =10 kDa) generated by pepsin digestion of Bet v 1a.

FIG. 5.2: unbound peptides (MW<=10 kDa) to the HSP, from the pepsin cleavage of Bet v 1a FIG. 5.3: pepsin generated-Bet v 1a peptides (MW<10 kDa), that were bound to the HSP.

Figure 6:
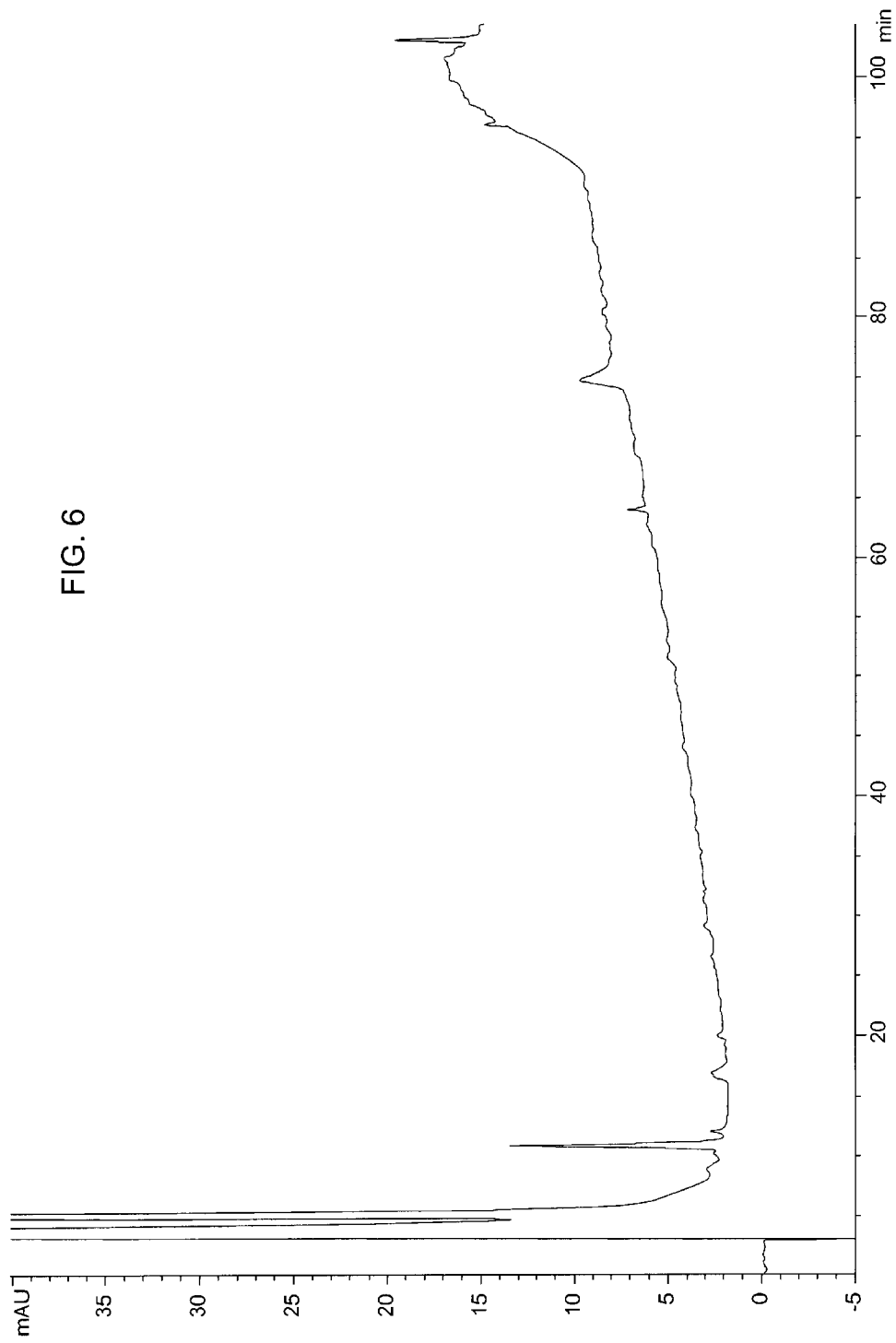

FIG. 6: chromatogram of any potential material, including ADP and/or ATP, bound to ATP-treated DnaK.

Example 2

Diagnosis Test Including a Mixture of Peptides Resulting from the Pepsin Digestion of Beta-lactoglobulin and *E. coli* HSP Pools of purified IgG from milk allergic children (Allergics) and from healthy controls (HC) were labeled with biotin and allowed to react with solid phase bound peptides. These peptides were obtained after pepsin digestion of beta lactoglobulin (BLG) and ultrafiltration (<10 kDa). Antibody binding was assessed with streptavidin-peroxidase conjugate, and appropriate substrate coloration.

Interference on the antibody binding was examined by mixing peptides (i.e. pepsin digested BLG=pB), HSP or HSP-pB mixture (w/w) together with the antibody solution.

The presence of peptides alone had no effect on the actual binding efficiency of Allergics or HC IgG. Neither GroEL alone nor GroEl -peptides complexes were inhibitors.

The presence of DnaK-pB complexes but not DnaK alone was inhibiting the binding of allergic IgG but not those from HC, indicating that conformational modifications of allergenic peptides through DnaK complex formation was competing with solid phase bound allergenic peptides for allergic IgG. Other results with DnaJ and GrpE were unconclusive here as both HSP alone or in peptide complexed form were inhibitors for both allergies and HC.

The DnaK example is demonstrating the potential use of HSP-peptide complexes in allergic diagnostic tests as discriminant from normal non allergic subjects.

Figure 7:
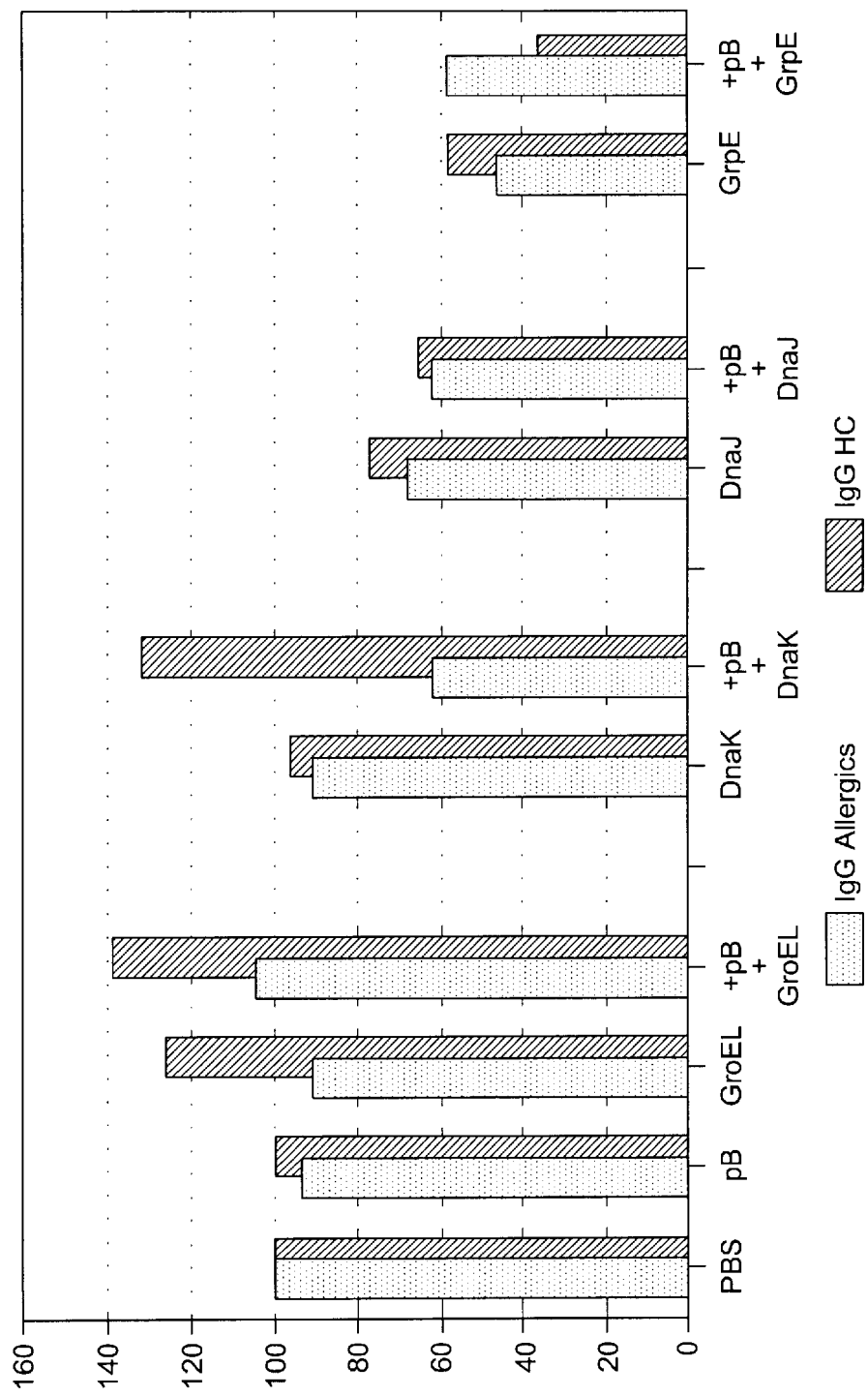

The enclosed FIG. 7 represents the relative % of binding efficiency of pools of purified IgG from milk allergic children (Allergics) and from healthy controls (HC), expressed as the ratio of the measured optical density in the presence of potential interfering substances and the control binding in the presence of the dilution buffer alone (PBS) (pB:peptides resulting from beta-lactoglobulin pepsin digestion (<10 kD). HSP were: GroEl, DnaK, DnaJ, GrpE as recombinant proteins from E. Coli. (+pB+HSP) are mixtures of peptides resulting from beta-lactoglobulin pepsin digestion (<10 kD) and the above mentioned HSP (w/w)).

Example 3

Antigenic Nature of HSP-Peptides Complexes

1. Betalactoglobulin

Peptides obtained from pepsin digestion of betalactoglobulin (BLG) and ultrafiltrated (<10 kD) were shown to remain antigenic in vitro as attested by their capacity to stimulate the lymphocyte proliferation of any sensitized human subject, in a similar way to that induced by the intact whole BLG molecule. Detectable levels of lymphocyte stimulation were obtained after 5 days cultures and assessed by H3 thymidine incorporation. The lowest stimulant concentration of BLG or its pepsin digested peptides fell to 10 ng/ml. Using a non stimulant concentration of DnaK (100 ng/ml) in culture, the admission to the mixture of pepsin digested peptides lowered the stimulant antigenic threshold by a factor of 10 (i.e. 1 ng/ml). This is indicating the adjuvant effect of DnaK when joined to sub threshold levels of antigen.

2. Allogenic Peptides

Membranes of lymphomononuclear cells were isolated from C3H mice spleens, homogenized, submitted to pepsin digestion and ultrafiltrated to keep peptides <10 kDa. When used as antigen to stimulate lymphocytes from the allogenic strain of Balc/c mice, their was no response at any tested concentration. Mixtures of these peptides with DnaK allowed a significative stimulation manifested by increased H3 thymidine incorporation, as could be induced by intact C3H cells. The response was not visible if the responding cells were of the same strain origin as the peptide donor. The specificity of these responses is entirely superposable to those of mixed lymphocyte cultures and excludes a role for any unspecific stimulation that could have occurred, as from the DnaK for example. Indeed DnaK alone was not stimulant. This is documenting that DnaK complexes are able to present allogenic peptides in an available form to responding lymphocytes, and that it renders possible to stimulate cells with a soluble form of antigens that are usually presented in a cellular form.

Example 4

Pharmaceutical Compositions

A. Basis of the Model Considered a) Using the Oral Route

Oral administration allows an induction of immunological tolerances, and is increasingly widely applied in the field of antiallergic desensitization. However, it requires the use of larger amounts of antigens than via the parenteral route, and has to extend over periods of at least several years (2, 3). Optimization of the dose administration regime and of their periodicity can be adapted by a person skilled in the art so as to avoid syndromic reactions (replication of the allergic symptomatology in the case of an overdose), which are frequent but not dangerous on account of the slow progression in the increase of the doses administered (2).

b) Using Peptide-stress Protein Complexes

Stress proteins (heat shock proteins (HSP)) constitute a series of protein families, which have been highly conserved during evolution from bacteria through to man, and which have the capacity to bind to peptides or to proteins whose conformational structure is altered or on course to its final conformation (4).

They have several roles, including participation in intracellular transport leading to polypeptide assembly for the synthesis of certain proteins or their elimination. Some are expressed at the surface of different cells and can contribute to the antigenic presentation, in particular to T lymphocytes to the receptors for antigen of gamma-delta type, which colonize the mucous membranes and lymphoid organs associated with the digestive mucosa.

The antigenic presentation via HSPs of the family HSP70, to gamma-delta ($\gamma$, $\delta$) T lymphocytes makes it possible to dispense with the presentation dependent on the type II major histocompatibility complex.

Parenteral injection of HSP-peptide complexes into experimental animals makes it possible to obtain a noteworthy adjuvant effect (5, 6) which determines or amplifies the antigenic power of these peptides.

Certain bacterial HSPs of the families HSP60 and HSP70 are the target of immune responses which have a protective role with regard to infection with these microorganisms.

It has recently been proposed to perform desensitization orally by giving peptide extracts of E. coli containing HSP60 to patients suffering from rheumatoid arthritis, with a certain beneficial effect (5, 6). Considering the negligible side effects, the authors propose to attempt the test on other inflammatory complaints in order to manipulate a response directed against one of these microbial HSPs itself, which is considered as an auto-antigen substitute.

The inventors have discovered, unexpectedly, that stress proteins constitute a noteworthy vector for presenting peptides to lymphoid systems of the digestive tract and inducing a tolerance. The stress proteins of saprophytic bacteria appear to be the ones which are the most abundant in nature in the digestive lumen. It is also probable that the peptides derived from the digestion of food constitute the most abundant mass of antigenic fragments available for the formation of HSP-peptide complexes. However, the abundance of the peptides generated, and the presumed limited amount of bacterial HSPs makes the formation of an immunologically efficient amount of these HSP-antigenic peptide complexes uncertain, and all the more so since the absorbed amount of antigen with desensitizing intent is very low (a few tens of $\mu$g) with regard to the food protein load.

The inventors have proposed to promote the formation of these complexes before arrival in the digestive tract, i.e. in vitro, by using purified E. coli stress proteins and peptides derived from the digestion of BLG with pepsin.

c) Using Tests of Competition Between Serum Antibodies and Monoclonal Antibodies for BLG The two monoclonal antibodies referred to below as M6 and M7 each recognize a different conformational epitope on the BLG molecule. Their different qualitative properties are used as recognition markers for single epitopes in a competition with all of an individual's serum antibodies. It emerges from clinical studies that symptomatic individuals and asymptomatic individuals recognize on this molecule epitopes which, for at least a part, are different (7), which are referred to below as epitopic profiles.

The epitope recognized by M6 is recognized particularly well by allergic and symptomatic individuals. Binding of the M6 antibody to intact BLG is actually better inhibited by the sera of children who are allergic to milk than by the sera of non-allergic individuals, whether these are children or adults in good health (blood donors).

The epitope recognized by M7 is better recognized by asymptomatic individuals than by allergic individuals. Binding of the M7 antibody to BLG is better inhibited by asymptomatic individuals than by allergic individuals.

Antigenic binding competitively against M6 is used as a specificity index representing the epitopic profile recognized by the allergic individuals, and in a complementary manner, the competition against M7 as a specificity index representing the epitopic profile recognized by the asymptomatic individuals.

Validation of this interpretation was confirmed longitudinally by clinical studies. The acquisition of a state of tolerance to milk is accompanied by a conversion of the fine specificity of the serum antibodies, toward the standard profile of asymptomatic individuals.

It is this epitopic discrimination expressed at the level of the circulating antibodies which serves here as an analytical tool for influencing oral antigenic modulation.

B. Experimental Model

Syngenic mice received, in their drinking water, very small amounts of peptides derived from the peptic digestion of beta-lactoglobulin (BLG), which were precoupled or otherwise with purified stress proteins and whose functional capacity was intact (capacity to bind to impaired peptides or proteins).

a) Animal Origin and Rearing Conditions 40 individuals 8 to 16 weeks old were taken from a rearing stock of Balbc mice fed for several generations on a diet poor in cow's milk: 13 $\mu$g of beta-lactoglobulin/gram of nutrient granules.

b) Preparation of the Antigenic Complexes

BLG was digested on contact with pepsin coupled to agarose (Sigma) under incomplete digestion conditions, and then filtered on a 10,000 dalton filter. The concentration of the digestion product (pB) was measured by spectrophotometry (yield of 30 to 50% of intact protein).

1 $\mu$g/ml phosphate buffer solutions (PBS) were incubated with 1 $\mu$g/ml solutions of the following *E. coli* stress proteins: DnaK, DnaJ, GroEL, GrpE (Stressgen) for at least one hour at ambient temperature. 1 ml aliquots of each combination were frozen.

c) Treatment Groups and Oral Posology of the Complexes

A solution of complexes (1 ml) was added, after thawing, to the 100 ml water bottle given daily to each cage of four mice. Each type of complex is administered to 8 mice. A control group receives the non-complexed pB antigen.

The solution was added 3 times a week for two weeks (i.e. six times), from time zero.

d) Antibody Response

An individual sample of blood was taken from the retro-orbital plexus at time zero and after 4 weeks. The animals are anaesthetized with ether and then exsanguinated, after 8 weeks.

The specificity of the serum antibodies was examined by an ELISA type competitive test.

e) Test of Antibody Specificity by Competition

Polystyrene multiwell plates are passively covered, by absorption at ambient temperature, with a small amount of BLG (0.3 $\mu$g/ml in bicarbonate buffer) and then saturated with gelatin (1%, weight/vol—Haemacel (R)).

The mouse serum is diluted 100-fold with dilution buffer (PBSdil) consisting of: PBS-EDTA (10 mM)—Tween 20 (0.05%)—gelatin (Haemacel—1%).

Two murine monoclonal antibodies produced were selected for their specificity with regard to conformational epitopes of BLG. They were biotinylated and are used at their limit dilution for antigenic binding, defined in the following way: the dilution which allows a maximum signal but which is sensitive to any reduction in the antigen load, at its specific dilution, and which can be competitively inhibited with a pool of sera from untreated mice. The reason for this is that the latter produce natural antibodies against BLG, in relation to exposure to the food antigen, even minimal exposure.

100 $\mu$l of diluted serum and of biotinylated antibody are mixed together in a well, in duplicate.

After incubation overnight at ambient temperature, the binding of the monoclonal antibody is measured by the proportional retention of biotin revealed by uptake of streptavidin coupled to horseradish peroxidase. This peroxidase colors an ortho-phenylenediamine substrate. The optical density (O.D.) is measured by spectrophotometry. The background noise (b.n.) is measured in antigen-free wells. The maximum binding is defined either in the absence of competition (monoclonal antibody alone) or in the presence of relatively non-inhibiting serum.

The results are expressed as a percentage of inhibition of binding of the monoclonal antibody by:

% inhibition=100×(test O.D.−b.n. O.D.)/(maximum O.D.−b.n. O.D.)

Figure 8:
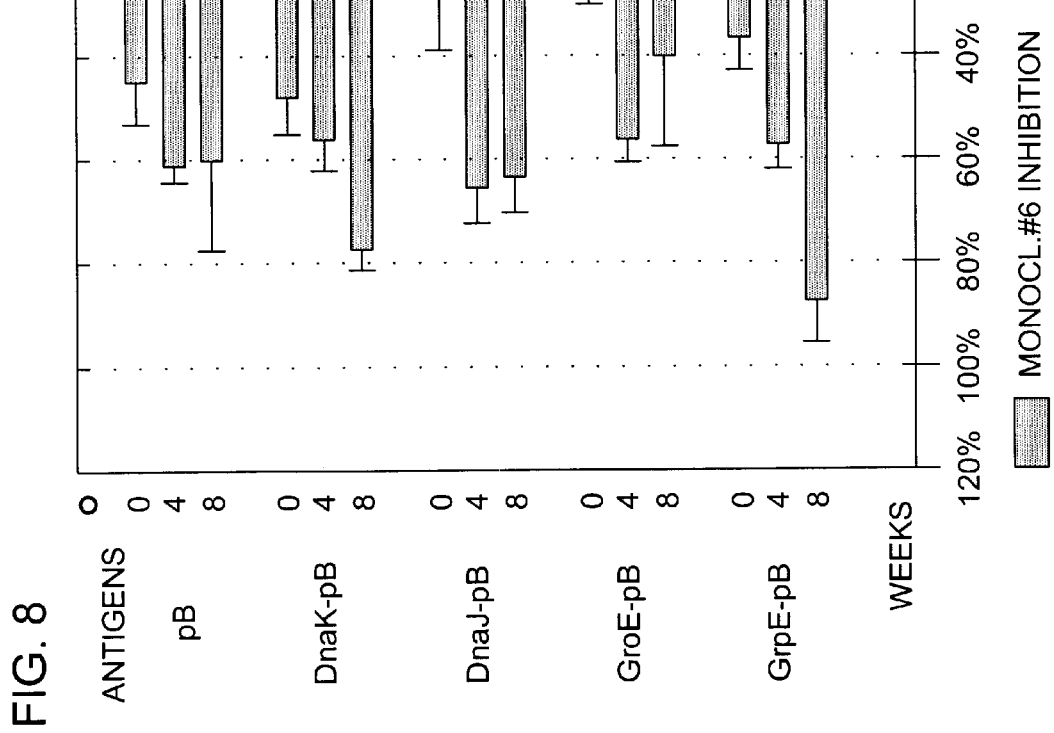

The correspondence between the profile of epitopes recognized on the antigen and the individual's clinical state (tolerance or otherwise) is confirmed by other examples:

model of allergy to acari:
the evolution of the fine specificity of anti-acari antibodies in allergic children shows the existence of an epitopic profile under the effect of the desensitization induced both parenterally and orally,
the evolution of the antibodies g) Results FIG. 8 summarizes the experimental data:

Inhibition of the M6 Antibody

The left-hand side shows the changes in the averages of inhibition (+standard deviation) of the binding of the M6 monoclonal antibody by the individual sera, for the various treatment groups.

The numerical data are compiled in Table 1.

The control group receiving the peptides digested with pepsin (pB) shows an increase in its average inhibition capacity from 45 to 60% and 59% after 4 and 8 weeks. This variation is significant ($p<0.05$—paired T test) relative to the start, but stable after 4 weeks.

For the group receiving the DnaK-pB complexes, this capacity rises from 48 to 56% and then 77% over the same period, the latter being greater than in the control group ($p<0.01$—non-paired T test) and very significant relative to the time zero ($p<0.001$—paired T).

Similarly, the groups receiving the complexes DnaJ-pB, GroEL-pB and GrpE-pB show a very significant increase after 4 weeks and which rises further at the eighth week (this value is considerably higher than the value of the control group for the complexes GroEL-pB and GrpE-pB at the corresponding moment).

Inhibition of the M7 Antibody

The right-hand side of FIG. 8 shows the changes in the averages of inhibition (+standard deviation) of the binding of the M7 monoclonal antibody, by the individual sera, for the various groups treated.

The numerical data are compiled in Table 2.

The control group receiving the BLG peptides digested with pepsin (pB) have an average inhibition capacity which falls from 70 to 52% and 57% in 4 and 8 weeks. This variation is significant (p<0.01—paired T test), although stable after 4 weeks.

For the group receiving the DnaK-pB complexes, this capacity already reduces significantly at the fourth week, falling from 68 to 51%, as in the control group.

However, the result collapses at 17% at the eighth week (p<0.001—paired T), which is markedly lower than that of the control group for the corresponding sample (p<0.01—non-paired T test).

The change is parallel to that for the group treated with the DnaJ-pB complexes.

For the group receiving GroEL-pB complexes, the reduction in the inhibitory power is immediately maximal, reaching 28% from the fourth week, and remains at the same level, 30%, at the eighth week.

In the group receiving GrpE-pB complexes the reduction in the inhibitory power is also immediately maximal, falling from 72 to 22% from the fourth week, but appears subsequently to diminish, returning to an average level of 41%.

h) Conclusion

The administration of peptides derived from the enzymatic digestion of a major milk antigen, in this instance beta-lactoglobulin, in the form of complexes associated with stress proteins according to the invention, and via the oral route, results in a radical and very rapid modification in the profile of the epitopes recognized by the circulating antibodies. These antibodies are naturally present in all the individuals exposed to the antigen via their food. In a model of mice, chronically exposed to a small amount of the antigen via this route, the dose of antigen administered over a brief period of time is very low, far below the amount ingested naturally (estimated at 0.25 µg per individual and per day of treatment in the form of complexes and 150 µg per individual and per day in the common diet).

The speed of the change is all the more noteworthy since the half-life of the serum antibodies, mainly IgGs, is 3 weeks, which means that at the eighth week, there should still be a quarter of the antibodies present at the end of the treatment of only 2 weeks. All the stress proteins used were efficient. In a second experiment with DnaK-pB complexes, an attempt to determine a lower limit dose was unsuccessful, despite the use of doses as much as 10 times lower (0.1 µg/100 ml bottle/3 days per week).

C. Orally Induced Tolerance With Regard to Major Histocompatibility Antigens

1. Experimental Model

Syngenic animals (Balbc mice) receive a protein preparation dissolved in their drinking water. It contains fragments of histocompatibility antigens from syngenic mice of another strain, any graft from which they would reject (C3H mice).

The tolerance-generating effect is expected to be enhanced when these fragments are combined with a bacterial stress protein (in this case Dnak from E. coli).

As a control, a group of mice receive, in the same manner, a complex of Dnak with peptide fragments similarly obtained from beta-lactoglobulin (major antigen of milk).

It should be expected that the oral sensitization would specifically attenuate the lymphocyte reactivity with regard to a strain of foreign lymphocytes of the same type as those used for the oral preparation and not with respect to an unrelated third strain.

2. Materials and Method a) Animals 3 groups of 12 mice are taken from a rearing stock of syngenic mice of Balbc strain are reared in cages of 6 animals. Each group receives, for 2 weeks, one of the following preparations in the bottle of drinking water at a rate of 3 distributions per week (every other day and not at the weekend) and a dose of 1 µg of complex per 100 ml of water:

- a complex of Dnak-beta-lactoglobulin peptides (control preparation)
- a solution of pepsin-digested spleen lymphocyte membrane peptides (containing fragments of histocompatibility antigens) from CH3 mice
- a complex of these peptides associated with purified Dnak from E. coli (Stressgen).

b) Test of Acquired Tolerance (In Vitro)

This test is based on a monodirectional mixed lymphocyte culture.

The responding cells are isolated from the spleen of the test animals. The lympho-monocyte cells are obtained after centrifugation on a density gradient with a ficoll-isopaque mixture (Pharmacia). They are resuspended using 4 million cells/ml in RPMI 1640 culture medium buffered with Hepes and with bicarbonate, supplemented with 2-mercaptoethanol, glutamine, geomycin and 10% calf serum.

The stimulating cells are obtained in the same way from mice of different strains, from their MHC: the C3H strain is a domestic (DOM) strain.

They are incubated for one hour in the presence of mitomycin in order to block their ability to multiply. They are then resuspended under the same conditions as the responding cells.

Lymphocyte Culture

An equal volume of suspension (0.1 ml) of responding cells and of stimulating cells are mixed, in triplicate, in round-bottomed wells of polystyrene multiwell culture plates in order to be subsequently incubated in an air/$CO_2$ (95/5%; vol/vol), humidified incubator at 37.5° C. for 5 days.

Each microculture well receives 2 µc of 2 C/mM tritiated thymidine (Amersham) 16 hours before stopping the culturing, which is carried out using a MASH II machine which filters each microculture on a glass-fiber membrane which retains the cell nuclei.

The nuclear radioactivity of each pellet, which reflects the de novo incorporation of thymidine into DNA, is measured by liquid scintillation counting (Packard Tricarb).

The results are expressed in counts per minute and represent the average of 3 samples of the same culture at the individual scale.

c) Experimental Procedure

The samples are taken at 2 different times:
- during the 3rd week following the start of the oral administration of one of the preparations,
- during the 7th week.

The animals are sacrificed 3 times per period.

Each culture experiment comprises 2 animals per group treated.

The mixed lymphocyte culture is prepared in parallel:
a) with respect to mitomycin-treated cells of C3H origin
b) with respect to mitomycin-treated cells of DOM origin d) Preparation of the Peptides Lymphocytes (20 million) of a suitable mouse strain are isolated from the spleen. This is a mixture of T and B lymphocyte in approximately equal amounts and thus bearing antigens of type I and II. They are treated with ultrasound (3×10 sec) and then centrifuged at 1000×g for 10 minutes. The supernatant is collected and recentrifuged in the same way. Next, the supernatant is centrifuged twice at 8000×g. The final supernatant is enriched in cell membranes and freed of cell nuclear debris and Golgi apparatus. It is then subjected to digestion with pepsin coupled to agarose beads, at pH 2 in glycine buffer, for 1 h 30 min at 37° C. After gentle centrifugation to separate the agarose beads, and neutralization at pH 7 with TRIS buffer, the mixture is filtered through a filter (Millipore, limit 10 kD). The yield is about 500 µg of peptide (determination by spectrophotometry) referred to as LMp.

A solution of 50 µg of peptide is mixed with a solution of 50 µg of Dnak (Stressgen) to form a Dnak-LMp complex.

The Dnak complex with beta-lactoglobulin peptide (Bp) is made in the same way using peptides derived from the peptic digestion of purified beta-lactoglobulin (cf. above).

3. Results

Figure 9:
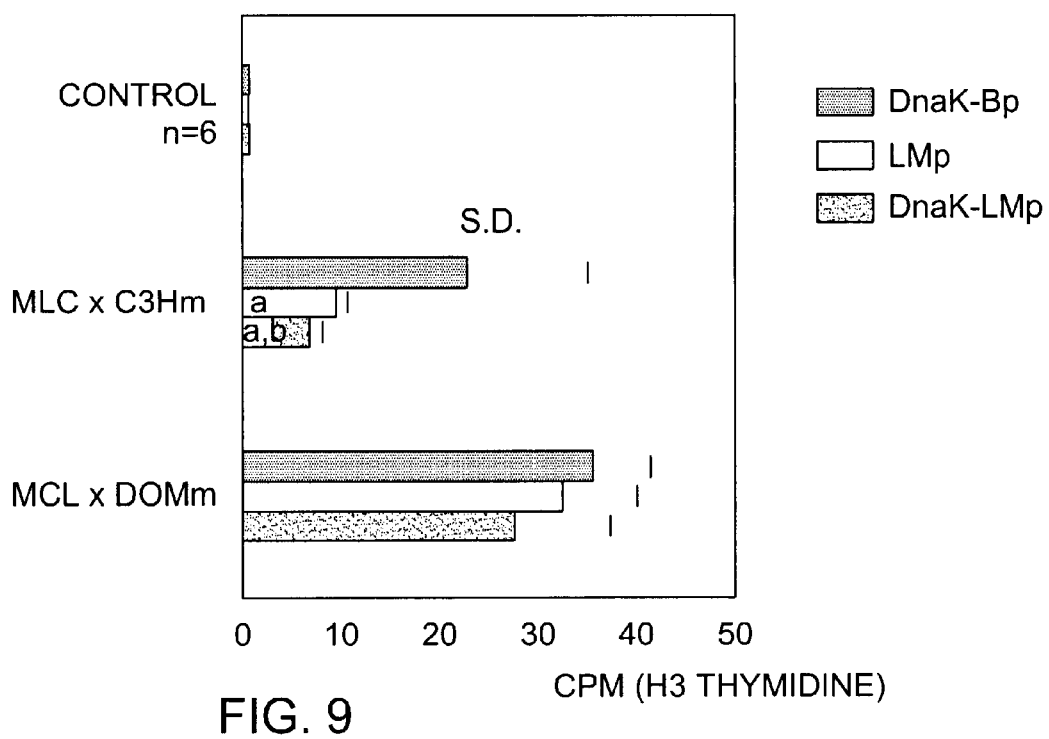

After treatment for 3 Weeks (FIG. 9)

The group of mice which received the Dnak-LMp complex responds the worst to the stimulation of mitomycin-treated C3H cells (C3Hm).

This is different ($p<0.02$; T-test) from the group which received the peptide LMp alone, and equal to that which received the Dnak-Bp control complex ($p<0.01$; T-test).

It should be noted, however, that administration of the peptide alone (without Dnak) also has an effect, since this group responds significantly less well than the control group ($p<0.01$; T-test).

However, the specificity of the response inhibition is guaranteed by the fact that the lymphocyte reactivity of the three groups is equivalent with regard to mitomycin-treated cells of a third, unrelated strain (DOMm).

Figure 10:
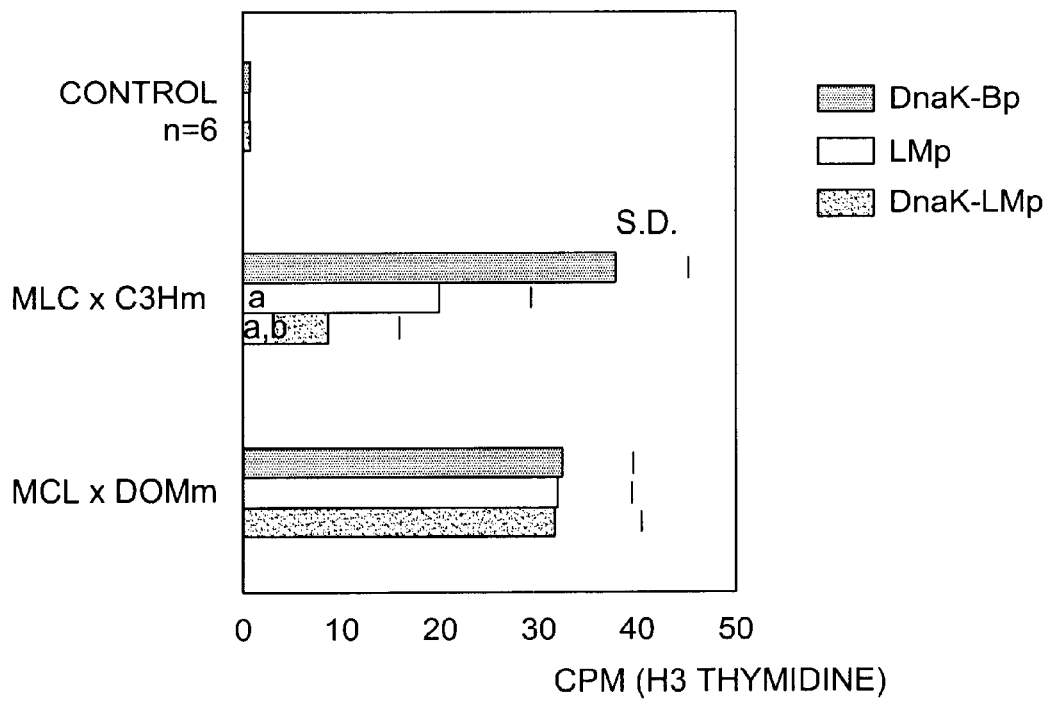

After 7 Weeks (FIG. 10), or 4 Weeks After Stopping the Oral Administration

The differences between the 3 groups remain quite pronounced. The group treated with Dnak-LMp is the most inhibited with regard both to the group which received the membrane peptide alone ($p<0.02$; T-test) and to the control group ($p<0.01$; T-test).

Administration of the peptide alone again allows an attenuation of response with respect to the control group ($p<0.01$; T-test).

The specificity of the response is once again verified by the parallel test with respect to mitomycin-treated cells of an unrelated strain (DOMm) and in which the 3 differently treated groups react in the same way.

The administration of peptides obtained by peptic digestion of spleen lymphocytes from mouse strains characterized by an incompatibility in the H-2 system both at the K and D levels and the A-E levels in extremely low amounts and for two weeks, has the effect of strongly attenuating the unconditional response of immunocompetent lymphocytes, in vitro, which usually indicates this incompatibility.

This attenuation is enhanced by the presentation of this type of peptide in the form of peptide-Dnak complexes.

This attenuation is specific and in no way reaches the capacity of response with regard to a different variety, which bears no relation to the strain used for the tolerization.

D. Tolerance of Syngenic Mice with Regard to a Graft of Allogenic Cells

1. Model and Experimental Scheme

Mouse Strains

Balbc for the animals made tolerant

C3H for the animals donating cells to be grafted (allogenic) and stimulating cells in mixed lymphocyte culture (MLC)

They are reared in cages of 6 animals. Each group consists of 12 animals per treatment.

The oral treatment is carried out according to the previous procedure.

Experimental Scheme

Complexes administered in the drinking water:

Days 0, 2, 4, 7, 9

Allogenic graft: $20 \times 10^6$ intraperitoneal C3H spleen cells: Day 16

Sacrifice, collection of spleens and culturing of the spleen cells:

15 weeks after the graft

Detection and Counting of the Allogenic Cells a) By the Presence of Cells Bearing MHC Type II Functional test in bidirectional syngenic mixed culture.

The spleen cells of treated and grafted mice are cultured with cells from untreated (naive) syngenic mice (Balbc).

Normally, there is no proliferative response to be expected if the content of the spleen cells of treated and grafted animals is composed solely of syngenic cells.

On the other hand, the presence of allogenic cells, signaling the in vivo taking of the graft, should result in a proliferation of MLC type by the so-called naive, intolerant cells, which is proportionately greater the larger the number of foreign cells.

In order to evaluate the order of magnitude of the taking of the graft, an attempt at relative quantification of the response is carried out with reference to a dose/response curve obtained by adding known and increasing amounts of C3H allogenic cells to an identical amount of naive and responding cells ($200 \times 10^3$ cells/well).

b) By the Presence of Cells Bearing MHC Type I

Direct counting by flow cytofluorometry immunofluorescence using a mouse monoclonal antibody specific for MHC type I of the C3H mouse: H-2 kk (Serotec), coupled to fluorescein or to phycoerythrin on a suspension of spleen cells.

2. Results

Figure 11:
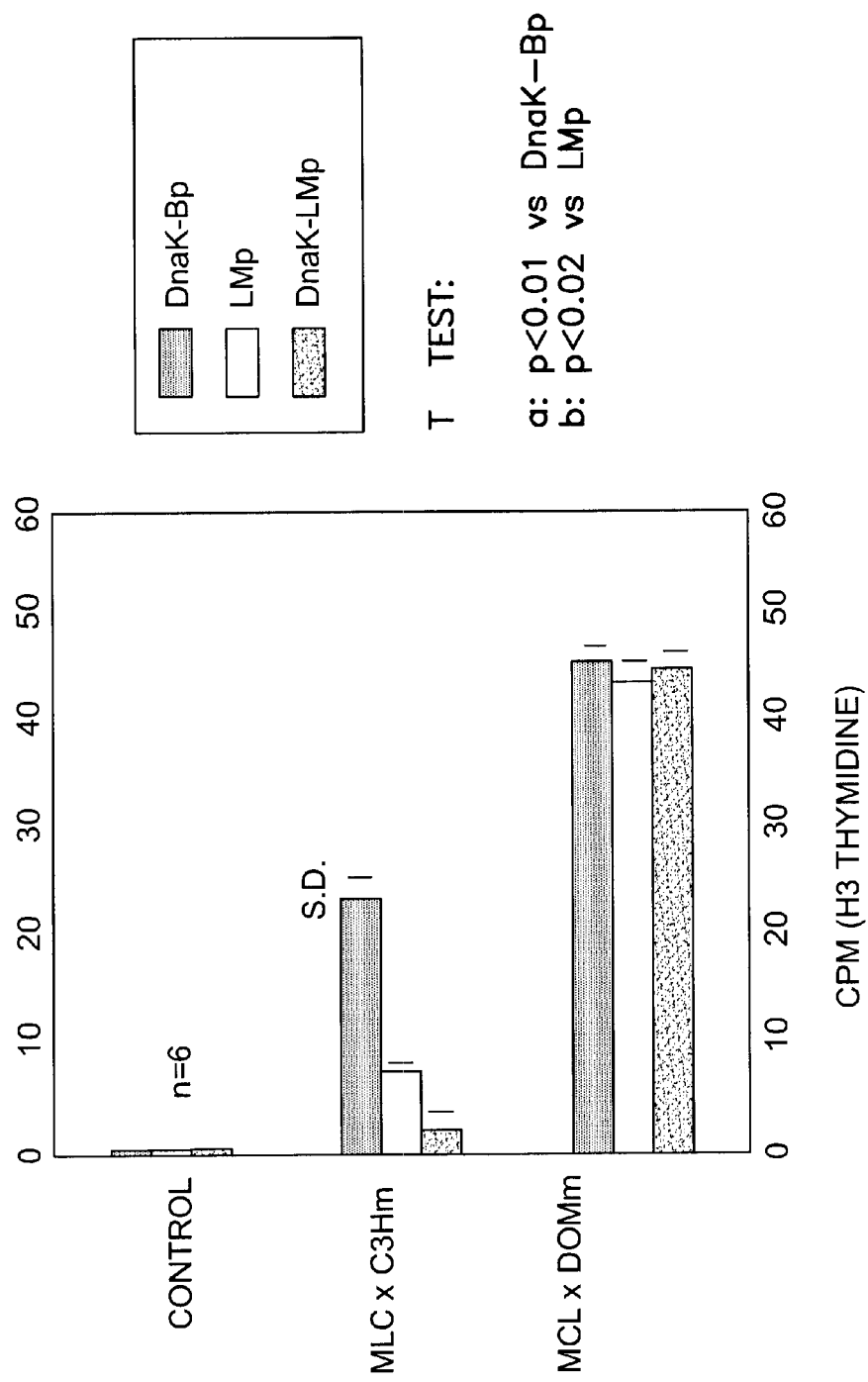

As seen in FIG. 11, 15 weeks after the peritoneal graft, the spleen cells of the group treated with DnaK-C3H mouse lymphomonocyte membrane peptide complexes are incapable of responding to stimulation with mitomycin-treated C3H cells. This is evidence of the induction of an allogenic tolerance.

The group treated with the peptide alone is also tolerated to a lesser extent.

The group treated with DnaK-beta-lactoglobulin peptide is not tolerant at all.

Moreover, the mixed cultures stimulated with another allogenic population, originating from a histoincompatible strain other than C3H, are all similar. This is evidence that no treatment has impaired or altered the MLC response capacity, and that the effect of the treatment is quite specific to the mouse strain from which the membrane peptides originate.

Figure 12:
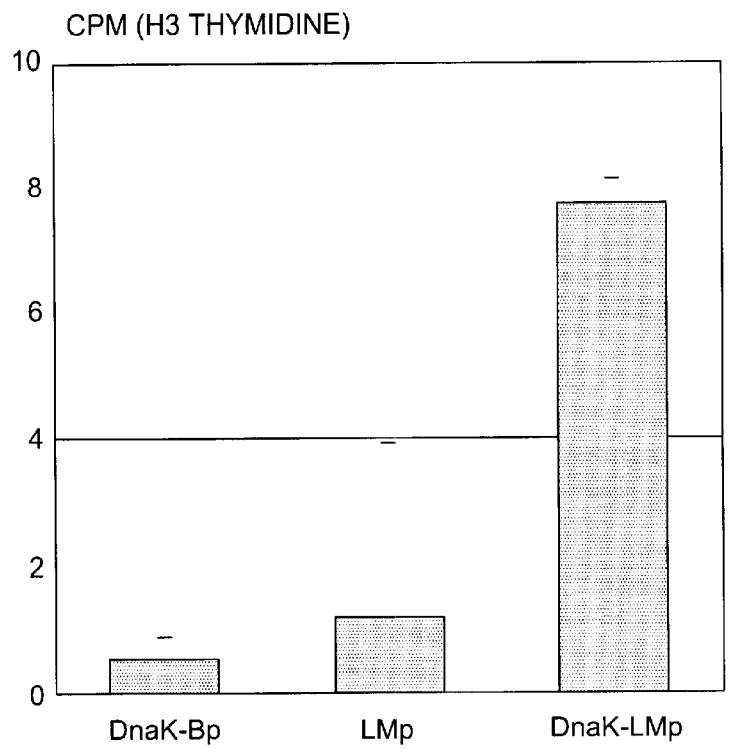

As represented in FIG. 12, the MLC response of cells from animals which are neither treated nor grafted is used to reveal the existence of foreign cells in a mixture of spleen cells from grafted animals, which would thus be of C3H origin in this case.

It appears that the spleens of mice treated orally before grafting with LMp and DnaK-LMp contain allogenic components since they give rise to a very significantly proliferative response which is different from the response of the control group treated with a DnaK-irrelevant peptide (beta-lactoglobulin) complex. The latter has a response which does not differ from the background noise.

Figure 13:
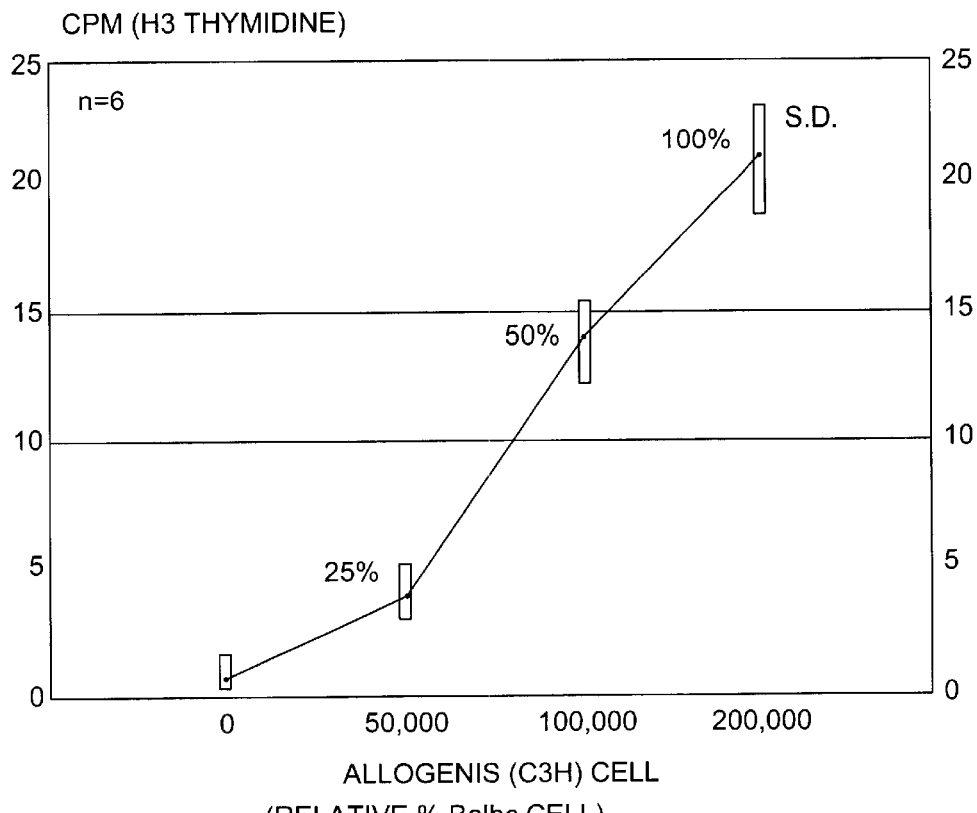

For comparative purposes, a series of mixed cultures were carried out in parallel with known and increasing amounts of C3H cells (FIG. 13). They give rise to a proliferative response which is proportional to the amount of foreign cells.

The average response level recorded with spleen cells from grafted animals and tolerized with DnaK-LMp complexes is thought to correspond to a content of about 30% of C3H cells.

The presence of cells of grafted type in the spleen is measured by immunofluorescence using an antibody which is specific for the MHC I of C3H (H-2kk) (Table 5). The group treated with DnaK-LMp contains 14.7% of this antibody on average, this value being significantly higher than that of the other two groups.

This presence of allo-antigens can only be observed providing that the grafted animal spleen cells are left to stand at 37° C. in the absence of serum, which suggests that it is essential to be able to re-express these antigens whose presence would thus be modified in vivo, quite probably by anti-H-2kk antibodies. This adds another mechanism of tolerance of the graft to the tolerance purely attributed to the responding T cells.

TABLE 1

Inhibitions of the M6 monoclonal antibody which binds nBLG by means of individual mouse sera: change as a function of time as a function of the type of complex administered orally.

| | | % of inhibition of the binding of M6 | | |
|---|---|---|---|---|
| | | Average | Standard deviation | Number of cases |
| Group 1: Control (dBLG only) | | | | |
| SAMPLE | 1 | 45.0100 | 8.4146 | 8 |
| SAMPLE | 2 | 60.6750 | 3.9304 | 8 |
| SAMPLE | 3 | 59.6338 | 17.4714 | 8 |
| Group 2: dBLG-DnaK complexes | | | | |
| SAMPLE | 1 | 48.4350 | 7.0540 | 8 |
| SAMPLE | 2 | 56.3675 | 5.6146 | 8 |
| SAMPLE | 3 | 77.0975 | 3.8966 | 8 |
| Group 3: dBLG-DnaJ | | | | |
| SAMPLE | 1 | 23.7350 | 15.3990 | 8 |
| SAMPLE | 2 | 65.7013 | 6.2958 | 8 |
| SAMPLE | 3 | 65.3863 | 4.7270 | 8 |
| Group 4: dBLG-GroEL | | | | |
| SAMPLE | 1 | 24.9538 | 4.7972 | 8 |
| SAMPLE | 2 | 56.0100 | 4.3929 | 8 |
| SAMPLE | 3 | 80.0287 | 1.9401 | 8 |
| Group 5: dBLG-GrpE | | | | |
| SAMPLE | 1 | 37.3313 | 6.4248 | 8 |
| SAMPLE | 2 | 56.6962 | 5.5641 | 8 |
| SAMPLE | 3 | 87.1525 | 7.8731 | 8 |

TABLE 2

Inhibitions of the M7 monoclonal antibody which binds nBLG by means of individual mouse sera: change as a function of time as a function of the type of complex administered orally.

| | | % of inhibition of the binding of M7 | | |
|---|---|---|---|---|
| | | Average | Standard deviation | Number of cases |
| Group 1: Control (dBLG only) | | | | |
| SAMPLE | 1 | 70.0658 | 3.5541 | 8 |
| SAMPLE | 2 | 52.8224 | 2.3458 | 8 |
| SAMPLE | 3 | 57.0592 | 7.8996 | 8 |
| Group 2: dBLG-DnaK complexes | | | | |
| SAMPLE | 1 | 68.9145 | 2.6698 | 8 |
| SAMPLE | 2 | 51.6908 | 3.0857 | 8 |
| SAMPLE | 3 | 17.2697 | 8.0473 | 8 |
| Group 3: dBLG-DnaJ | | | | |
| SAMPLE | 1 | 78.4276 | 3.4832 | 8 |
| SAMPLE | 2 | 50.8553 | 3.9778 | 8 |
| SAMPLE | 3 | 26.9145 | 3.2069 | 8 |
| Group 4: dBLG-GroEL | | | | |
| SAMPLE | 1 | 73.9671 | 3.1679 | 8 |
| SAMPLE | 2 | 28.5132 | 8.6072 | 8 |
| SAMPLE | 3 | 30.2829 | 14.2174 | 8 |
| Group 5: dBLG-GrpE | | | | |
| SAMPLE | 1 | 72.8355 | 4.7722 | 8 |
| SAMPLE | 2 | 22.2961 | 9.5040 | 8 |
| SAMPLE | 3 | 41.3684 | 6.4331 | 8 |

TABLE 3

Anti (native) nBLG antibody titers after logarithmic transformations: change as a function of time as a function of the type of complex administered orally.

| | | Ln of titers (A.U.) | | |
|---|---|---|---|---|
| | | Average | Standard deviation | Number of cases |
| Group 1: Control (dBLG only) | | | | |
| SAMPLE | 1 | 3.8526 | .4547 | 8 |
| SAMPLE | 2 | 4.2162 | .3395 | 8 |
| SAMPLE | 3 | 4.2059 | .2946 | 8 |
| Group 2: dBLG-DnaK complexes | | | | |
| SAMPLE | 1 | 3.9738 | .7957 | 8 |
| SAMPLE | 2 | 4.3749 | .6353 | 8 |
| SAMPLE | 3 | 3.2562 | .5057 | 8 |
| Group 3: dBLG-DnaJ | | | | |
| SAMPLE | 1 | 3.7073 | .4435 | 7 |
| SAMPLE | 2 | 4.1348 | .5475 | 8 |
| SAMPLE | 3 | 4.3917 | .5047 | 8 |
| Group 4: dBLG-GroEL | | | | |
| SAMPLE | 1 | 4.3714 | .4215 | 8 |
| SAMPLE | 2 | 3.6419 | .4704 | 8 |
| SAMPLE | 3 | 3.9964 | .2724 | 8 |
| Group 5: dBLG-GrpE | | | | |
| SAMPLE | 1 | 4.1526 | .6401 | 8 |
| SAMPLE | 2 | 4.1739 | .4464 | 8 |
| SAMPLE | 3 | 3.6126 | .4873 | 8 |

TABLE 4

Differences in inhibition between the binding
of the M6 and M7 antibodies to nBLG:

| | | % of inhibition of the binding of M6 − % of inhibition of the binding of M7 | |
|---|---|---|---|
| | Average | Standard deviation | Number of cases |
| Group 1: Control (dBLG only) | | | |
| SAMPLE 1 | −25.0558 | 9.0035 | 8 |
| SAMPLE 2 | 7.8526 | 5.6470 | 8 |
| SAMPLE 3 | 2.5745 | 19.8676 | 8 |
| Group 2: dBLG-DnaK complexes | | | |
| SAMPLE 1 | −20.4795 | 8.5253 | 8 |
| SAMPLE 2 | 4.6767 | 6.1131 | 8 |
| SAMPLE 3 | 59.8278 | 9.2686 | 8 |
| Group 3: dBLG-DnaJ | | | |
| SAMPLE 1 | −54.6926 | 13.8705 | 8 |
| SAMPLE 2 | 14.8460 | 6.4665 | 8 |
| SAMPLE 3 | 38.4718 | 5.6903 | 8 |
| Group 4: dBLG-GroEL | | | |
| SAMPLE 1 | −49.0134 | 3.9824 | 8 |
| SAMPLE 2 | 27.4968 | 10.6337 | 8 |
| SAMPLE 3 | 49.7459 | 14.6732 | 8 |
| Group 5: dBLG-GrpE | | | |
| SAMPLE 1 | −35.5043 | 4.8959 | 8 |
| SAMPLE 2 | 34.4002 | 13.4093 | 8 |
| SAMPLE 3 | 45.7841 | 8.7931 | 8 |

TABLE 5

Persistant allogenic cells (H-2kk +) in the
spleens of Balbc mice grafted with C3H cells:
Oral treatment

| DnaK-Bp | Lymphocyte membrane peptide (LMp) alone | DnaK-LMp |
|---|---|---|
| 1.0% | 0.9% | 14.2% |
| 1.5 | 2.8 | 25.0 |
| 0.5 | 3.6 | 9.2 |
| 0.5 | 3.7 | 10.4 |
| Average ET | Average ET | Average ET |
| 0.9%  0.5 | 2.7%  1.3 | 14.7%  7.2 |

Coupled T-tests:
DnaK-LMp/DnaK-Bp: p = 0.026
DnaK-LMp/LMp: p = 0.052

References

1. Patterson, R. et al., *Allergy Proc.*, Vol. 15 (5), pp. 239–264 (1994)
2. Ferrick, D. A., *Mak-TW Tolerance and Self-Reactivity in V gamma 1.1 C gamma 4 transgenic mice*
3. Staines, U. et al., J. Rheumatol., Vol. 54 (3), pp. 145–154 (1995)
4. Polla, B. S. et al., *Clin. Exp. Allergy*, Vol. 23 (7), pp. 548–556 (1993)
5. Healy, A. M. et al., Ann. N. Y. Acad. Sci., Vol. 663, pp. 319–330 (1992)
6. Revillard, J. P. et al., *Dev. Biol. Stand.*, Vol. 77, pp. 31–37 (1992)
7. Bousquet, J. et al., *Allergy*, Vol. 49, pp. 31–36 (1994)

What is claimed is:

1. A process for the preparation of a composition comprising at least one conformational or sequential epitope of an antigenic structure of a major histocompatability locus of type I or type II comprising the steps:

(a) in-vito hydrolysis of a major histoaompatabiuty locus of type I or type II; and
    (b) mixing with one or more stress proteins.

2. The process according to claim 1, wherein said at least one conformational or sequential epitope of an antigenic structure of a major histocompatability locus of type I or type II has a molecular weight inferior or equal to 10 kD.

3. The process according to claim 1, wherein the in-vito hydrolysis is an enzymatic hydrolysis.

4. The process according to claim 1, wherein said at least one stress protein is a bacterial heat shock protein.

5. The process according to claim 4, wherein said bacterial stress protein is selected from the group consisting of DNAK, DNAJ, GroEL or GrpE heat shock proteins.

6. Composition comprising at least one stress protein and at least one conformational or sequential epitope of an antigenic structure of a major histocompatability locus of type I or type II.

7. Composition according to claim 6, wherein said at least one stress protein is a bacterial heat shock protein.

8. Composition according to claim 7, wherein said bacterial heat shock protein is selected from the group consisting of the DNAK, DNAJ, GroEL or Grpe heat shock proteins.

9. Pharmaceutical or food composition comprising the composition of claim 6 and an adequate pharmaceutical or food vehicle.

10. Pharmaceutical or food composition according to claim 9, wherein said pharmaceutical or food composition is adequate for oral administration.

11. The process according to claim 1, wherein the at least one conformational or sequential epitope of an antigenic structure of a major histocompatability locus of type I or type II is a peptide.

12. Composition of claim 6, wherein said at least one conformation or sequential epitope of an antigenic structure of a major histocompatability locus of type I or type II is a peptide.

13. Composition of claim 6, wherein said at least one conformation or sequential epitope of an antigenic structure of a major histocompatability locus of type I or type II is prepared by in-vitro hydrolysis of a major histocompatability locus of type I or type II.

14. Composition of claim 13, wherein said at least one conformational or sequential epitope of an antigenic structure of a major histocompatibility locus of type I or type II has a molecular weight of 10 kD or less.

15. A method of treating a graft rejection comprising the step of administering a composition comprising at least one stress protein and at least one conformational or sequential epitope of an antigenic structure of a major histocompatability locus of type I or type II.

16. The method of claim 15, wherein said at least one stress protein is a bacterial heat shock protein.

17. The method of claim 16, wherein said bacterial heat shock protein is selected from the group consisting of the DNAK, DNAJ, GroEL or GrpE heat shock proteins.

18. The method of claim 15, wherein said at least one conformation or sequential epitope of an antigenic structure of a major histocompatability locus of type I or type II is a peptide.

19. The method of claim 15, wherein said at least one conformation or sequential epitope of an antigenic structure of a major histocompatability locus of type I or type II is prepared by in-vitro hydrolysis of a major histocompatability locus of type I or type II.

20. The method of claim 19, wherein said at least one conformational or sequential epitope of an antigenic-structure of a major histocompatability locus of type I or type II has a molecular weight of 10 kD or less.

* * * * *